(12) United States Patent
Eastwood et al.

(10) Patent No.: US 11,730,505 B2
(45) Date of Patent: Aug. 22, 2023

(54) FLEXIBLE ARTICULATE SURGICAL TOOL

(71) Applicant: THE HOSPITAL FOR SICK CHILDREN, Toronto (CA)

(72) Inventors: Kyle W. Eastwood, Carlisle (CA); Peter Francis, London (CA); Thomas Looi, Markham (CA); Hani E. Naguib, Toronto (CA); James M. Drake, Toronto (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 191 days.

(21) Appl. No.: 16/468,042

(22) PCT Filed: Dec. 18, 2017

(86) PCT No.: PCT/CA2017/051532
§ 371 (c)(1),
(2) Date: Jun. 10, 2019

(87) PCT Pub. No.: WO2018/107300
PCT Pub. Date: Jun. 21, 2018

(65) Prior Publication Data
US 2020/0015839 A1 Jan. 16, 2020

Related U.S. Application Data

(60) Provisional application No. 62/435,439, filed on Dec. 16, 2016.

(51) Int. Cl.
*A61B 17/29* (2006.01)
*A61B 17/32* (2006.01)
(Continued)

(52) U.S. Cl.
CPC .... *A61B 17/320016* (2013.01); *A61B 17/295* (2013.01); *A61B 2017/0034* (2013.01);
(Continued)

(58) Field of Classification Search
CPC .......... A61B 17/320016; A61B 17/295; A61B 2017/00309; A61B 2017/00314;
(Continued)

(56) References Cited

U.S. PATENT DOCUMENTS 5,507,297 A * 4/1996 Slater ................. A61B 18/1445
606/205
2003/0023142 A1 1/2003 Grabover
(Continued)

OTHER PUBLICATIONS

P. J. Swaney, P. A. York, H. B. Gilbert, J. Burgner-Kahrs, and R. J. Webster III, "Design, Fabrication, and Testing of a Needle-sized Wrist for Surgical Instruments," ASME J. Med. Devices, No. c, 2016.
(Continued)

*Primary Examiner* — Kathleen S Holwerda
(74) *Attorney, Agent, or Firm* — Hill & Schumacher

(57) ABSTRACT

A flexible elongate shaft assembly which includes an elongate flexible tube having at least one joint built into the elongate flexible tube, and the at least one joint comprised of at least one notch. Each notch includes a contact-aided compliant notch topology built into the elongate flexible shaft configured to cause each notch to mechanically interfere with itself and self-reinforce during bending of each notch resulting in an increase in stiffness of each notch to prevent buckling and plastic deformation of the elongate flexible shaft assembly, and assume a predetermined and designed bending shape of the elongate flexible shaft assembly. The flexible elongate shaft assembly is incorporated into a flexible articulate surgical tool that provides the needed stiffness in order to be able to manipulate tissue and bear loads in anatomically confined spaces. The surgical tool includes a clinician operated handle, the flexible elongated shaft assembly extending from the handle to a surgical tool with the flexible elongate tube having one or more joint
(Continued)

sections located near the surgical tool. A flexible cable connects the handle to the surgical tool. The joint sections are configured so that when the clinician activates the surgical tool, a mechanical interference is generated in each of the notches and this mechanical interference not only increases stiffness throughout the articulation of the notch's range-of-motion but it also serves the dual purpose of controlling the bent "shape" of the flexible portion of the notch.

33 Claims, 19 Drawing Sheets

(51) Int. Cl.
  *A61B 17/295* (2006.01)
  *A61B 17/00* (2006.01)
(52) U.S. Cl.
  CPC ............ *A61B 2017/00309* (2013.01); *A61B 2017/00314* (2013.01)
(58) Field of Classification Search
  CPC ............ A61B 2017/0034; A61B 17/29; A61B 17/00234; A61B 2017/2901; A61B 2017/2905; A61B 2017/2908; A61B 1/0055; A61M 25/0133; A61M 25/0136; A61M 25/0138; A61M 25/0141; A61M 25/0144; A61M 25/0147; A61M 25/0053; A61M 25/0013
  See application file for complete search history.

(56) References Cited

U.S. PATENT DOCUMENTS

| | | |
|---|---|---|
| 2005/0273085 A1 | 12/2005 | Hinman et al. |
| 2009/0043372 A1 | 2/2009 | Nortiirop et al. |
| 2010/0312056 A1 | 12/2010 | Galperin et al. |
| 2014/0228748 A1* | 8/2014 | Rosenman ........ A61M 25/0138 604/95.04 |
| 2015/0094656 A1* | 4/2015 | Salahieh ........... A61M 25/0141 604/95.04 |
| 2016/0100745 A1 | 4/2016 | Seto et al. |
| 2016/0345947 A1 | 12/2016 | Salaiiieii et al. |
| 2016/0346513 A1* | 12/2016 | Swaney ............ A61B 17/3417 |

OTHER PUBLICATIONS

H. Fischer, B. Vogel, W. Pfleging, and H. Besser, "Flexible distal tip made of nitinol (NiTi) for a steerable endoscopic camera system," Mater Sci. Eng. A, vol. 273-275, pp. 780-783, 1999.
J. Peirs, H. Van Brussel, D. Reynaerts, and G. De Gersem, "A Flexible Distal Tip with Two Degrees of Freedom for Enhanced Dexterity in Endoscopic Robot Surgery," in The 13th Micromechanics Europe Workshop, 2002, pp. 271-274.
Y. Haga, Y. Muyari, S. Goto, T. Matsunaga, and M. Esashi, "Development of Minimally Invasive Medical Tools Using Laser Processing on Cylindrical Substrales," Electr. Eng. Japan, vol. 176, No. 1, pp. 65-74, 2011.
M. D. M. Kutzer, S. M. Segreti, C. Y. Brown, R. H. Taylor, S. C. Mears, and M. Armand, "Design of a New Cable-Driven Manipulator with a Large Open Lumen: Preliminary Applications in the Minimally-lnvasive Removal of Dsteolysis," in IEEE International Conference on Robotics and Automation, 2011, pp. 2913-2920.
S. C. Ryu, P. Renaud, R. J. Black, B. L. Daniel, and M. R. Cutkosky, "Feasibility Study of an Optically Actuated MR-compatible Active Needle," in IEEE International Conference on Intelligent Robots and Systems, 2011, pp. 2564-2569.
D. Wei, Y. Wenlong, H. Dawei, and D. Zhijiang, "Modeling of Flexible Arm with Triangular Notches for Applications in Single Port Access Abdominal Surgery," in IEEE International Conference on Robotics and Biomimetics, 2012, pp. 588-593.
J. A. Bell, C. E. Saikus, K. Ratnayaka, V. Wu, M. Sonmez, A. Z. Faranesh, J. H. Colyer, R. J. Lederman, and O. Kocaturk, "A Deflectable Guiding Catheter for Real-Time MRI-Guided Interventions," J. Magn. Reson. Imaging, vol. 35, No. 4, pp. 908-915, 2012.
J. Liu, B. Hall, M. Frecker, and E. W. Reutzel, "Compliant articulation structure using superelastic NiTiNOL," Smart Mater. Struct, vol. 22, No. 9, 2013.
N. Lobontiu, M. Guilin, T. Petersen, J. a Alcazar, and S. Member, "Planar Compliances of Symmetric Notch Flexure Hinges☐: The Right Circularly Corner-Filleted Parabolic Design," vol. 11, No. 1, pp. 169-176, 2014.
P. A. York, P. J. Swaney, H. B. Gilbert, and R. J. Webster III, "A Wrist for Needle-Sized Surgical Robots," in IEEE International Conference on Robotics and Automation, 2015, pp. 1776-1781.
J. Matern, G. Kuttler, C. Giebmeyer, P. Waller, and M. Faist, "Ergonomic aspects of five different types of laparoscopic instrument handles under dynamic conditions with respect to specific laparoscopic tasks: an electromyographic-based study.," Surg. Endosc., vol. 18, No. 8, pp. 1231-1241, 2004.
International Search Report of the parent PCT application PCT/CA2017/051532 dated Apr. 23, 2018.

\* cited by examiner

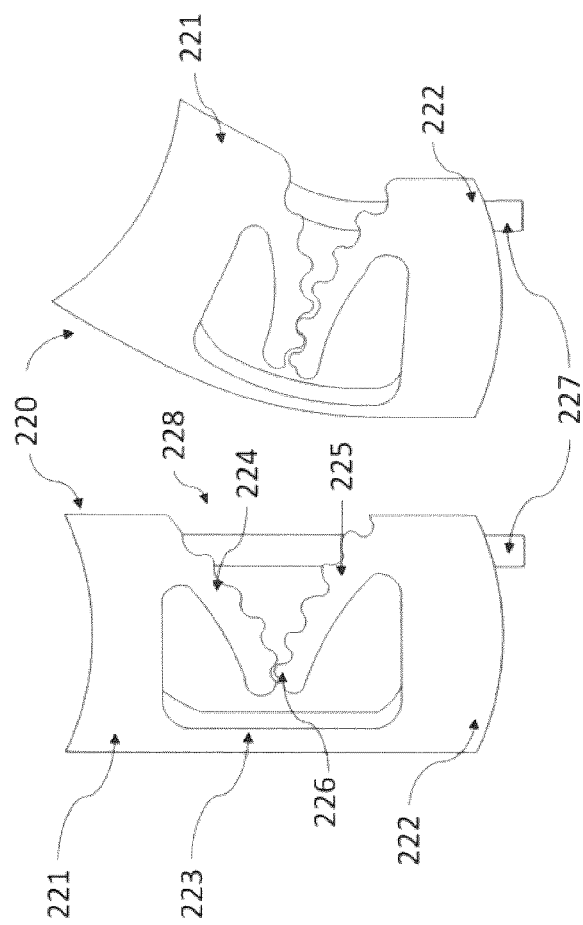

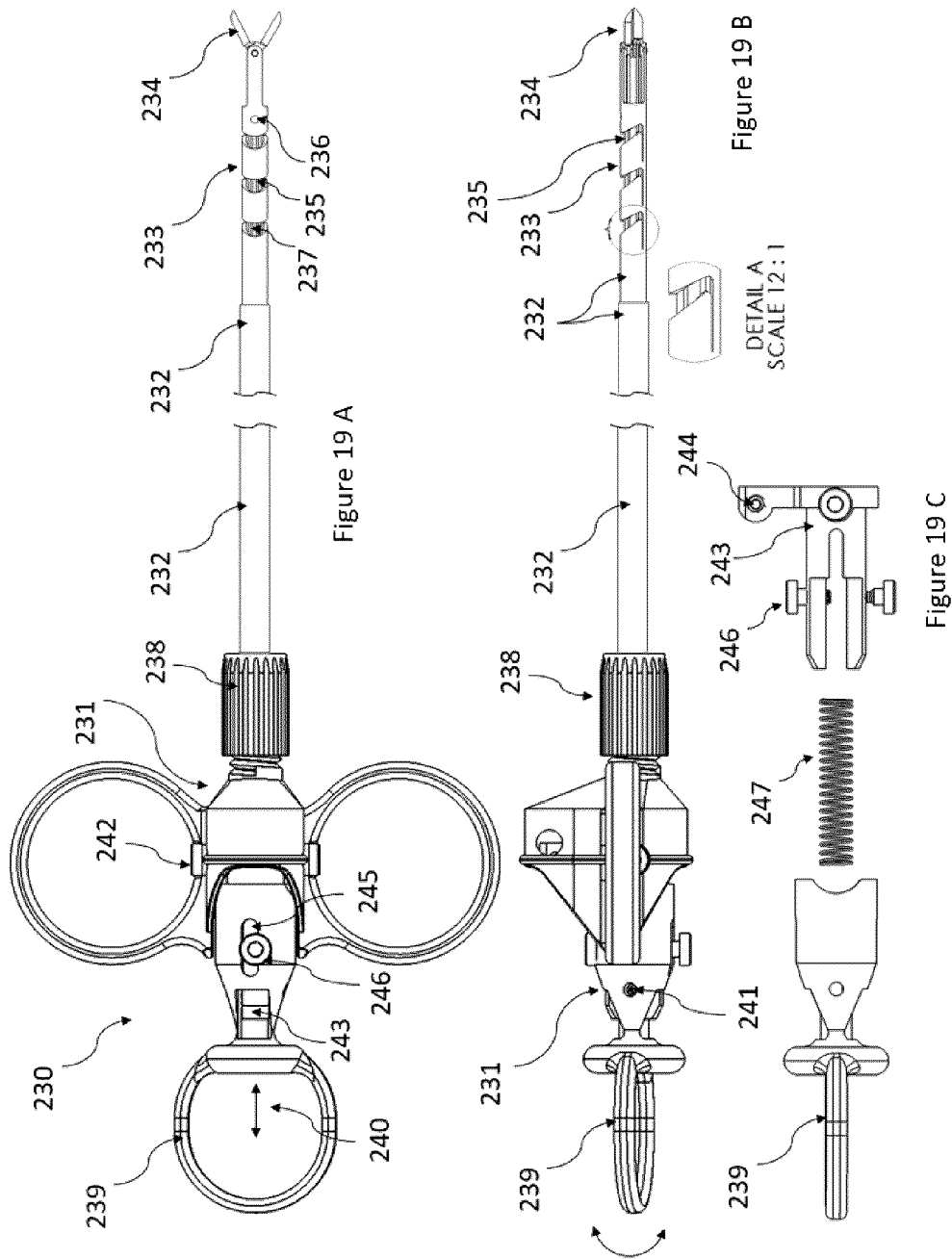

FLEXIBLE ARTICULATE SURGICAL TOOL

FIELD

This disclosure relates to a flexible elongate shaft assembly which is incorporated into an articulate surgical tool that provides the needed stiffness in order to be able to manipulate tissue and bear loads in anatomically confined spaces.

BACKGROUND

Current instruments used in minimally invasive neurosurgery (known as neuroendoscopy) are straight and rigid or slender and flexible with minimal control over the tool tip. As such, the range of motion and variety of tasks that can be performed using these instruments is limited to simple straight-line approaches, such as biopsy or the removal of small tumors within a direct line-of-sight from the surgeon's entry point. For more complex procedures which require significant freedom over the location of the tool's tip, the only existing options involve more invasive open surgeries and large craniotomies.

Neurosurgeons have attempted more complicated maneuvers using standard neuroendoscopic equipment with the goal of expanding the scope of neuroendoscopy to other procedures currently performed using more invasive microsurgery. However, in many cases, the limited reach and range-of-motion of standard neuroendoscopy equipment limits its application. From these attempts, there is a well-defined need and published call for new instruments that function more similarly to wrist-like laparoscopic tools. The major limitation to addressing this problem is the scale of the body cavities and anatomy within the head and neck. These spaces in which surgeons must operate are very small and delicate compared to the chest, abdomen and pelvis. New instruments must be compact enough to fit inside these body cavities without dominating the space and blocking the view of the camera. Further, these miniature instruments must be strong enough to manipulate tissue without bending or deforming.

One class of existing technology that attempts to address the need for working in small volumes is notched tube compliant mechanisms. An example of such a design is shown in FIG. 1. FIG. 1 shows a constrained workspace 200 with a notched tube joint 205. The size scale of the joint 205 is similar to the size scale of the workspace 200 and therefore the space 202 that the joint 205 occupies, while bending, would ideally be as small as possible. To achieve this goal, the joint radius 203 and the joint length 204 should be minimized.

FIGS. 2A to 2C shows the actuation of this mechanism. Here, a tube 10 made from a super-elastic material (such as nitinol) has rectangular shaped cuts or notches 12 cut into it. The remaining material at these notches 12 act like flexible hinges that can be bent without permanent deformation by applying a downward force on the inside of the tube 10 (using a cable, rod or other applied pressure).

When designing these types of joints for use in particularly small volumes as shown in FIG. 1, where the geometric size of the instrument 205 is on a similar order of magnitude as the surgical workspace 200, ensuring that the joint is compact is of paramount importance. Typically, this goal is approached by designing the mechanism's bent configuration 201 so that it occupies as little space 202 as possible. Cutting the tube asymmetrically (from one side inward as shown in FIG. 1 and FIGS. 2A to 2C) is often preferred because the notch folds into itself as it bends, and the notch's overall length shortens. Increasing the depth of cut 206 (FIG. 1) has the largest impact on how sharp a bending radius of curvature 203 the notch can attain in order to stay within the elastic strain region of the material. The sharpest achievable bends occur when the radius of bending of the notch 203 approaches the same value as the outer radius of the tube. To achieve this range of sharp bending, the cut depth becomes very deep, often exceeding 80% of the diameter of the tube for asymmetric notches. In these situations, the notch, and overall joint consisting of multiple notches, has excellent range-of-motion and compactness, but the overall "stiffness" of the notch, or its ability to support loads, is severely diminished. This value of 80% is based upon simulations which have been carried out by the present inventors.

In the case of asymmetric notch tubes, the directional stiffness in the front-back (FIG. 2A) directions is decreased by one or two orders of magnitude compared to an un-notched tube of equivalent size and material. The method which actuates the notch, causing it to bend (cable etc.), can counteract external loads applied from the front of the notch however there is no method to counteract the forces applied from the back of the notch. This limitation hinders the practical use of these asymmetric designs, despite their advantages, since tissue manipulation requires the joint stiffness to be above a certain application-specific threshold in all directions.

There are many surgical applications in the head and neck that could significantly benefit from notched tube joint mechanisms to increase the dexterity of surgical instruments. The present inventors contemplate that one of the main reasons this technology has not been employed for these applications is because with current designs, the stiffness is too low to manipulate tissue and bear loads.

Another approach which aims to improve the compactness of symmetric and asymmetric notched tube joints involves reducing the total number of notches and the width of the spacing between notches, see reference [1]. In doing so, designers aim to ensure that the total joint length needed to achieve the desired bending angle is distributed between the fewest number of individual notches possible, resulting in fewer, longer notches. One limitation for this design is the onset of buckling when the ratio of the notch width to notch length becomes too small. Where the notch width is the difference between the tube diameter and the notch cut depth. If individual notches become too long, they exhibit bending behavior that is difficult to predict and undesirable. The present inventors also contemplate that one of the main barriers to constructing truly compact notched-tube compliant joints is the need to limit the relative length of individual notches when their widths become very small, again resulting from deep cuts.

While FIG. 1 shows the tube in which the cuts 12 have been removed just from one side of the tube, (asymmetric), tools have been produced in which the tube has been provided with slots in a symmetrical design as depicted in FIG. 3. Specifically, FIG. 3 show published notched tube cutting topologies (references [2]—[11]) with the "basic" asymmetric notch shape of FIG. 1 shown in the left most image.

SUMMARY

The present disclosure provides a joint mechanism that is intended for working in small volumes. One application for the use of such a technology is in neurosurgery. Specifically, endoscope guided minimally invasive neurosurgery, referred to as neuroendoscopy. This technology is also relevant in any application where the dimensions of the work volume approach the same order of magnitude as the cross-sectional dimensions of the joint itself.

The present disclosure provides a flexible elongate shaft assembly, comprising:

an elongate flexible shaft having at least one joint built into the elongate flexible shaft, the at least one joint comprised of at least one notch with each notch having an internal section contact-aided compliant notch topology within each notch configured to cause each notch, upon bending, to mechanically interfere with itself and self-reinforce prior to being fully bent resulting in an increase in stiffness of each notch prior to being fully bent and to prevent buckling and plastic deformation of the elongate flexible shaft, and assume a predetermined and designed bending shape of the at least one joint and hence the elongate flexible shaft.

The flexible elongate shaft may be an elongated tube having a longitudinal axis, and wherein the contact-aided compliant notch topology comprises a notch with a generally transverse notch segment extending from a first side of the elongated tube towards an opposed second side of the elongated tube and terminating at a predetermined termination position adjacent to, and spaced from, the second side of the elongated tube, the generally transverse notch segment dividing the elongated tube into a proximal tube section located on one side of the generally transverse notch segment and a distal tube section located on the other side of the generally transverse notch segment, an elongated notch segment extending from the generally transverse notch segment at the predetermined termination position in a direction generally parallel to the longitudinal axis to define a flexible outer strip tube section along the opposed side of the elongated tube connecting the proximal and distal tube sections, and wherein the elongated notch segment has a preselected width such that upon movement of the distal tube section, relative to the proximal tube section, in a direction from the second side towards the first side, an inner surface of the flexible outer strip tube section adjacent to the elongated notch section segment comes into physical contact with an internal section of the proximal tube section adjacent to both the predetermined termination position and the elongated notch segment causing the at least one notch to mechanically interfere with itself and self-reinforce throughout range-of-motion of the notch.

The width of the elongated notch segment may be selected to give a predetermined amount of bending of the distal tube section with respect to the proximal tube section prior to the inner surface of the flexible outer strip tube section adjacent to the elongated notch segment coming into physical contact with the internal section of the proximal tube section.

The generally transverse notch segment extending from the first side of the elongated tube towards the opposed second side of the elongated tube may be tapered from a first opening size at the first side of the elongated tube down to a second opening size at the predetermined termination position such that the first opening size is greater than the second opening size, and wherein the first opening size is selected such that an end section of a distal tube section located on the first side of the elongated tube adjacent to the tapered notch and an end section of a proximal tube section located on the first side of the elongated tube adjacent to the tapered notch come into contact only at the end of a range-of-motion of each notch such that when the end section of the distal tube section located on the first side of the elongated tube adjacent to the tapered notch and the end section of the proximal tube section located on the first side of the elongated tube adjacent to the tapered notch come contact each notch cannot bend anymore, and wherein the first opening size is selected to ensure contact occurs just before a flexible part of each notch reaches any plastic deformation.

Thus, the present disclosure provides a contact-aided compliant notch topology used as a joint built into an elongate flexible shaft. The shaft may be comprised of one or multiple joints, and the joints one or multiple notches. The notch topology is configured so that the notch undergoes mechanical interference with itself through a majority of the notch's range-of-motion, in a manner that reinforces the notch to increase the notch's stiffness. The notch topology comprises both compliant and rigid regions that come in contact and reinforce each other to guide the bending shape of the compliant region and to reduce buckling of the compliant region. The design aims to address the trade-off between notched-tube compliant joints' range of motion and stiffness, while also ensuring a compact form factor. The invention includes incorporating contact-aided compliant notches onto a tube-shaft, or onto a curved surface. The invention includes combining the contact-aid features with mechanical-limit features that prevent overbending of the notch and plastic deformation.

The mechanical interference built into each notch not only increases stiffness throughout the articulation of the notch's range-of-motion but it also serves the dual purpose of controlling the bent "shape" of the flexible portion of the notch.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 2A to 2C show views of a Prior Art surgical tool design with an asymmetrically notched tube compliant joint in which, FIG. 2A shows the joint design initially bending from a small amount of tension applied to the actuation cable;

FIG. 2B shows the design further bending from more applied cable tension, and

FIG. 2C shows the joint fully articulated once the elastic strain limit of the material is reached.

FIGS. 9A and 9B indicate some ways in which the notches can be combined to produce more complex joints.

FIG. 18A shows an alternative exemplary flexible articulate surgical tool notch topology in the unbent position with processes extending from a proximal and distal tube section adjacent to the elongate notch segment. Each of these processes include teeth complementary to one another that mechanically interfere while sliding, pivoting and rolling, and act to reinforce the notch and guide the notch's bending shape.

FIG. 18B shows the notched tube of FIG. 18A in a bent configuration showing the teeth meshing with each other and the notch rigid.

FIG. 19A shows top view of an alternative handle design 230 where a middle ring handle 239 is articulated in a push-pull motion to open and close the end-effector, and is rolled about the pin joint 242 to apply tension to a proximal end of flexible cable.

FIG. 19B shows a side view of the tool of FIG. 19A that illustrates the shape of the notches included in the flexible instrument shaft 232.

FIG. 19C shows an exploded view of a sub-assembly of the handle in FIGS. 19A and 19B. Here, the arrangement of the ring handle 239, the compression spring 247 and the handle gimbal 243 can be seen.

DETAILED DESCRIPTION

Figure 1:
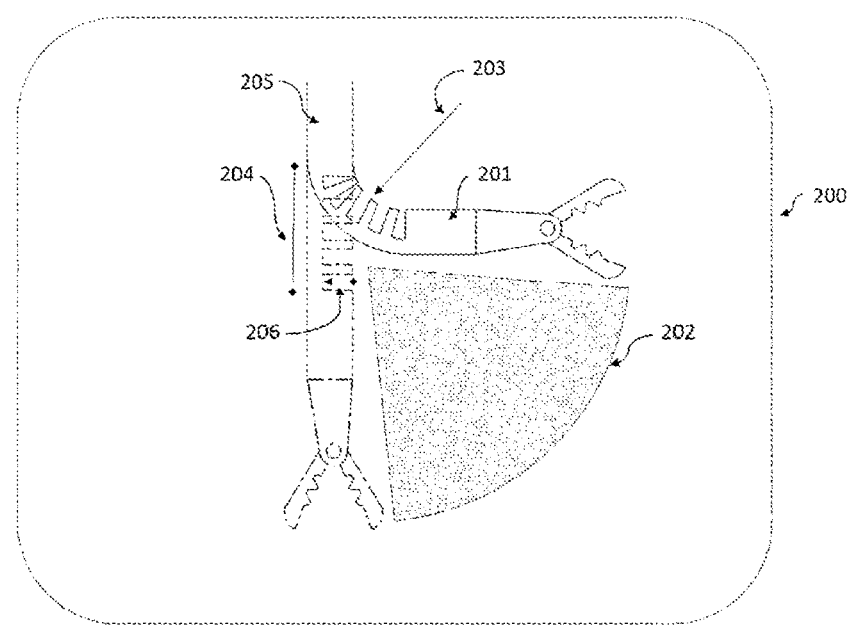
FIG. 1 shows a constrained workspace 200 with a notched tube joint 205.

Various embodiments and aspects of the disclosure will be described with reference to details discussed below. The following description and drawings are illustrative of the disclosure and are not to be construed as limiting the disclosure. The drawings are not necessarily to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

The present disclosure addresses the above-noted loss of "stiffness" throughout the notch's range-of-motion and provides a notch with the ability to support higher loads as it articulates, wherein its range-of-motion remains comparable to an equivalently sized rectangular notch.

The basic concept disclosed herein is a joint made from a single material which is notched in a configuration which utilizes physical interactions throughout the range of motion of the notch to increase stiffness along the primary cutting plane. This result can be achieved using various approaches to be described hereinafter. The approach disclosed herein relates to shaping the notch such that the flexible portion of the notch that makes up the "hinge" is reinforced by other rigid sections of the notch. This concept can be achieved by various means.

First, the flexible portion of the notch that makes up the "hinge" comes into physical contact at one or multiple points with a more rigid section of the notch. In this manner, the notch "mechanically interferes" with itself and self-reinforces the tube as it articulates through its range-of-motion. Expressed in other terms, one may consider the prior art "basic" notch design shown in FIG. 2 as a simply supported beam that is rigidly fixed at its base and has a bending moment applied to its tip by means of a cable, wire, rod, or pressure (pneumatic or hydraulic). The topology disclosed herein breaks from this convention in that the presently disclosed designs may be thought of as providing 3-point or multi-point bending configurations. In these embodiments, the flexible portion of the notch may slide or pivot around support points that are connected to more rigid portions of the notch. Put another way, multiple rigid regions of the notch are in contact with the flexible portion of the notch "in parallel", or "in series" or a combination thereof, to reinforce while at the same time not significantly limiting the range-of-motion of the notch as it bends.

Figure 5:
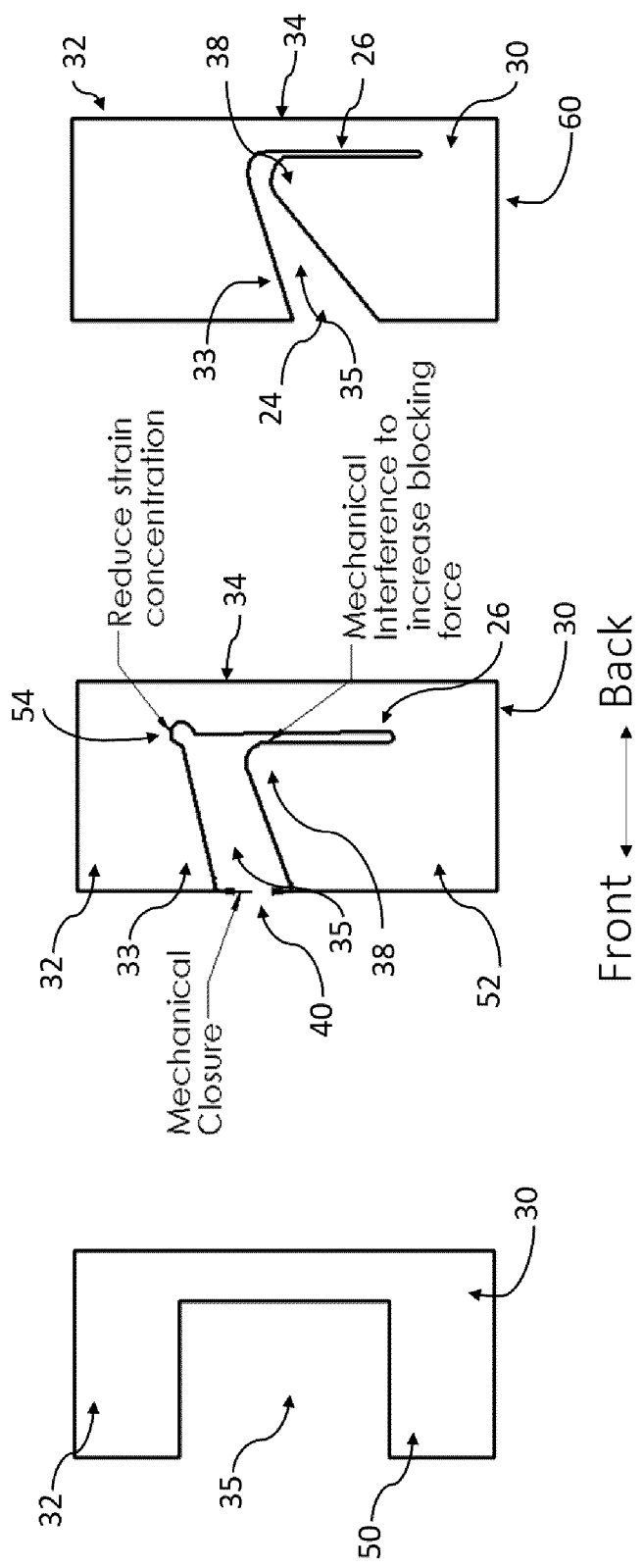
FIG. 5 shows a comparison of notch profiles with the left panel being a prior art design, the middle panel being an embodiment showing the basic concept for a contact-aided compliant notch topology as disclosed herein and the right panel showing a variation of the center panel design.
Figure 6:
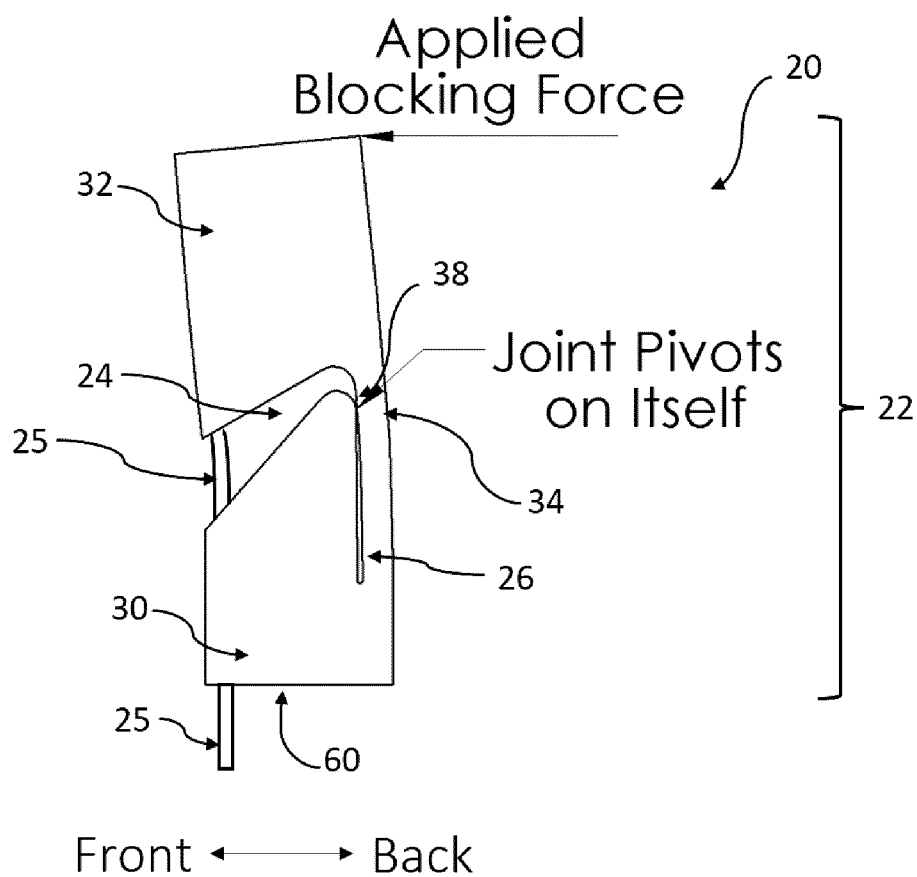
FIG. 6 shows a pivoting notched tube constructed in accordance with the present disclosure showing pivoting action in mechanical interference combined with mechanical closure.

FIG. 6 depicts the motion of a single notch in a portion of a flexible articulate surgical tool which shows one joint sub-section 20 of the tube 22 which includes a transverse notch segment 24 extending from the outer wall of the tube 22 which connects to generally parallel notch segment 26 which has the shape of an elongate channel which is substantially parallel to the longitudinal axis of the tube portion 22. It will be appreciated that the tube 22 may include more joint sub-sections 20. The presence of the transverse notch segment 24 extending a significant way through the tube 22, divides the tube into sections 30 and 32. These sections are connected by a flexible outer strip section 34 such that the distal tube section 32 (which leads to the end of the tube that connects to the surgical tool tip, not shown) can move with respect to the proximal tube section 30 as the flexible outer strip section 34 bends. By cutting the notch segments 24 and 26 as shown in FIG. 6, the tube section 32 can bend in the same way that the "basic" prior art shaped notch of FIG. 2 can bend but it has increased stiffness when external forces from the back to front direction are applied to the upper section 32 as seen in FIG. 6. This increased stiffness occurs because the flexible outer strip tube section 34 of tube portion 22, which undergoes bending almost immediately, comes into contact with the inner section 38 of the tube 22. In this manner, the joint "mechanically interferes" with itself and self-reinforces. This geometry does not limit the normal articulation of the flexible outer strip section 20. Although the shape that the bent flexible outer strip section 34 takes on during bending could be different than the shape of the bent flexible outer strip section in joint 50 shown in FIG. 5.

Figure 3:
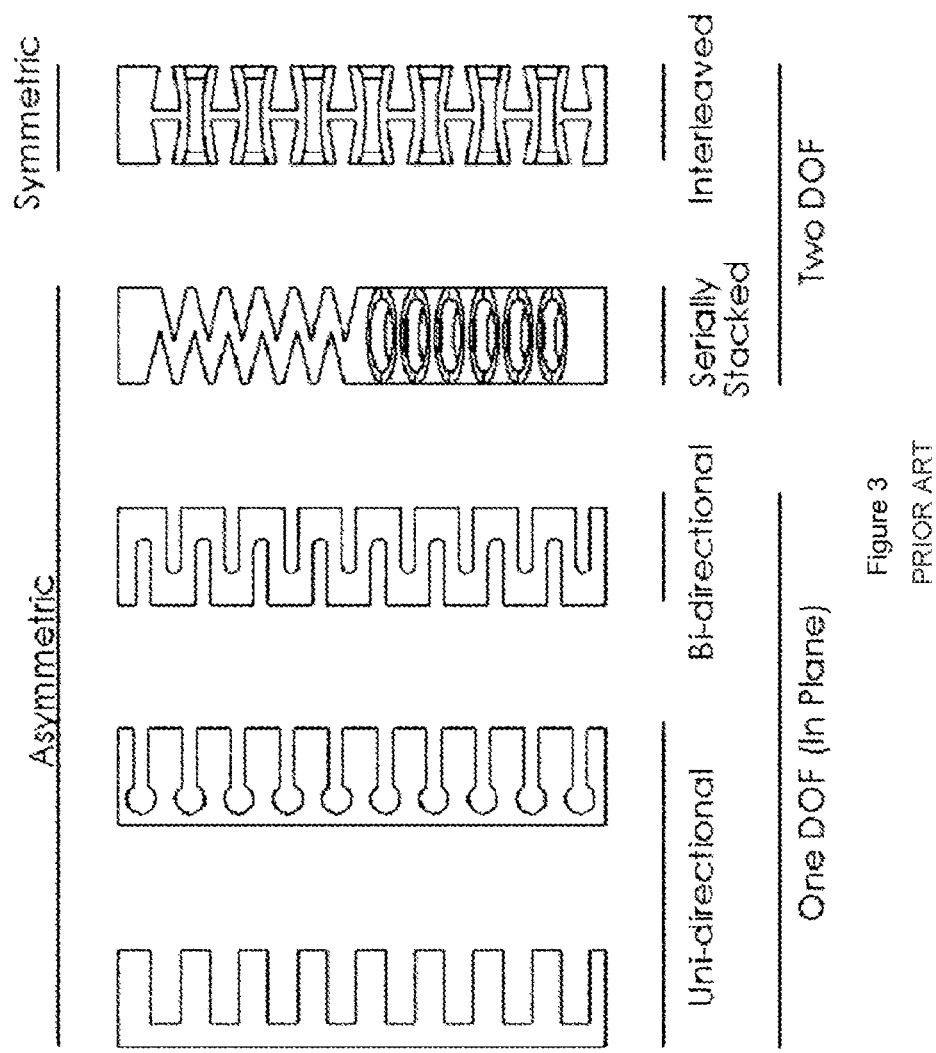
FIG. 3 shows published notched tube cutting topologies as disclosed in references [2] to [11] with the "basic" asymmetric notch shape of FIG. 1 and FIG. 2 shown in the left most image. Here, DOF is an acronym for degrees-of-freedom.
Figure 11:
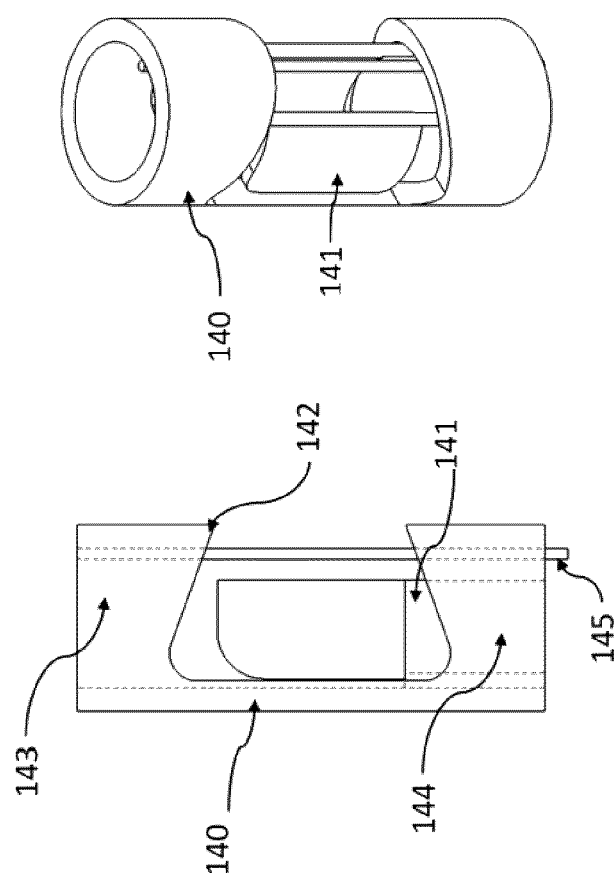
FIG. 11A is a side elevation view of an alternative flexible articulate surgical tool notch topology showing a notched tube section 140 with a tapered rectangular notch topology similar to those shown in FIG. 3. The mechanical reinforcement is provided by a separate tube 141 assembled concentrically inside of 140.
FIG. 11B is a perspective view of the notch topology of FIG. 11A.

It will be understood that the mechanical interference could also be created by configuring the joint to interfere with another, separate rigid component within, surrounding or attached to the flexible portion of the joint. For example, FIGS. 11A and 11B show a notched tube section 142 with a tapered rectangular notch topology similar to those shown in FIG. 3. FIG. 11A shows a transparent view of a notched tube which consists of a flexible outer strip section 140 and an upper rigid section 143 and lower rigid section 144. Through the transparent view, a separate rigid tube component 141 can be seen to be assembled concentrically within the notched tube. From FIG. 11B, it will be appreciated that the flexible outer strip section 140 will interfere with 141 during its range-of-motion when the actuation cable 145 is shortened. The interference between 140 and 141 is such that the rigid tube component 141 will mechanically reinforce the flexible outer strip section 140 but is not made from the same material or is a part of tube 140.

Figure 2:
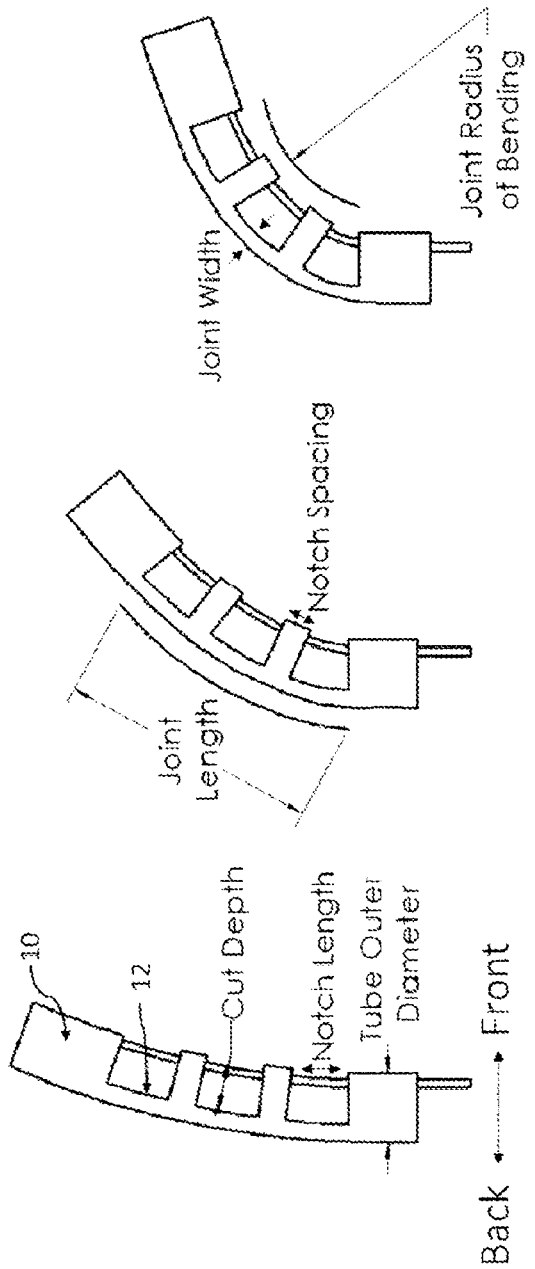

FIG. 5 shows a progression of the surgical tool compliant: joint notch profiles with the left panel being the prior art design of a rectangular-notch joint section 50, the same profile as shown in FIG. 2, the middle panel being an embodiment of a notched joint section 52 as disclosed herein showing the basic concept for a flexible tool and the right panel showing a joint section 60 which is a variation of the center panel design shown at 52 that has been refined to reduce strain concentrations. All three notch configurations 50, 52 and 60 consist of a proximal tube section 30 connected to a compliant flexible outer strip tube section 34 which is connected to a distal tube section 32. The transverse notch segment 35, representing space where tube material was removed to create the flexible outer strip tube section 34 has tapered edges 33 in the middle and right panels. These tapered edges are constructed such that the distance 40 (middle panel) and 24 (right hand side panel) are just far enough that the top and bottom edges of the notch come into contact before the onset of plastic deformation in the flexible outer strip tube section 34 or adjacent tube sections 30 or 32. This design feature is referred to as Mechanical Closure and has been demonstrated in the prior art depicted in FIG. 3.

The elongated notch segment 26 in the present notch designs in the center and right-hand side panel is a thin cut segment separating the flexible outer strip tube section 34 from the rigid tube reinforcement section 38 attached to the proximal tube section 30. The elongated notch segment 26 is designed such that the flexible outer strip tube section 34 is free to bend and rotate when an actuation force is applied to the internal top left side of the tube section 32 as shown in FIG. 6 where the actuation cable 25 is used to apply the bending force. The elongated notch segment 26 is further designed such that the flexible outer strip tube section 34 is inhibited from moving laterally if a force is applied perpendicular to 34 in the back to front direction. The notched structure in tube section 52 (FIG. 5) includes a circular cut-out 54 where the upper corner of transverse notch segment 35 terminates at the upper right corner of the notch and this provides for reduced strain concentration at this corner during articulation of the upper section 32 with respect to the lower section 30. For the notch 60, this feature is included into the transition from the generally transverse notch segment 35 to the elongated notch segment 26.

An important feature of the topology of the notches disclosed herein is the inclusion of a section of a part of the notch that is intended to create "mechanical closure." The main concept of mechanical closure is selecting cutting parameters while producing the notches that ensure the notch's edges come into contact during articulation, to limit its full range of motion, before the material's strain limit is reached. This feature improves the life-time of the notch because it prevents "over-bending" and permanently deforming the notch. It also allows the notch to fully close when it is in its maximum bending position which helps to make the notch "stiffer" when it is at its full range-of-motion. This feature is distinct from mechanical interference because mechanical interference increases the stiffness of the notch throughout its entire range-of-motion, not just at the end. Mechanical closure is also important because it addresses uneven loading of many notches placed in series. Consider the prior art notch joint of FIGS. 2A, 2B and 2C, where all three square notches are the same size and shape. Here, it can be observed that the notch closest to the bottom of the image, where the cable tension is being applied, closes more than the notch closest to the joint's tip. Mechanical closure ensures that once the first notch closes, the subsequent notches can fully close as more cable tension is applied, without risking over bending the first notch.

Figure 4:
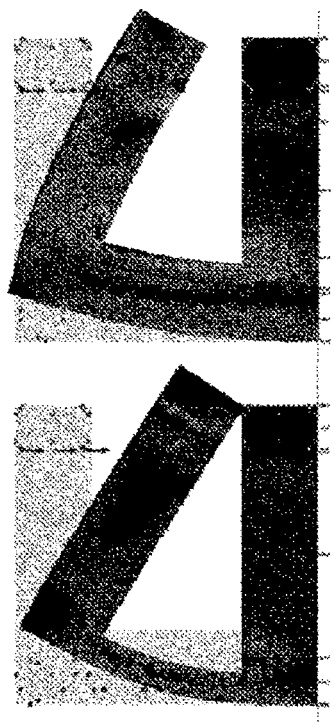
FIG. 4 shows the mechanical closure of a square "basic" prior art notch [left panel] compared to a different square notch that cannot mechanically close because it would plastically deform before the edges contact. This figure illustrates the need for modifying the shape of the notch to ensure the opposing edges of the notch come into contact before the elastic strain limit of the notch material is reached. If the "basic" notch shown in the [right] image were to be further articulated to that its edges came into contact, it would become permanently deformed. Some examples of how the shapes of notches have been modified to address this issue are shown in FIG. 3.

FIG. 4 depicts two square prior art notch designs which further describe the concept and importance of "mechanical closure". The prior notch shown on the left side of the figure can completely close compared to the differently sized and shaped square notch on the right side of FIG. 4 that cannot mechanically close because it would plastically deform before the edges contact. There are a subset of square notch geometry designs where this is possible, depending on the elastic strain limit of the material the notch is made from. In most cases, square notches cannot close on themselves without permanently deforming. To address this issue, the top and bottom edges of the notches are typically either tapered or "T" shaped, as shown in some of the designs in FIG. 3.

Figure 10:
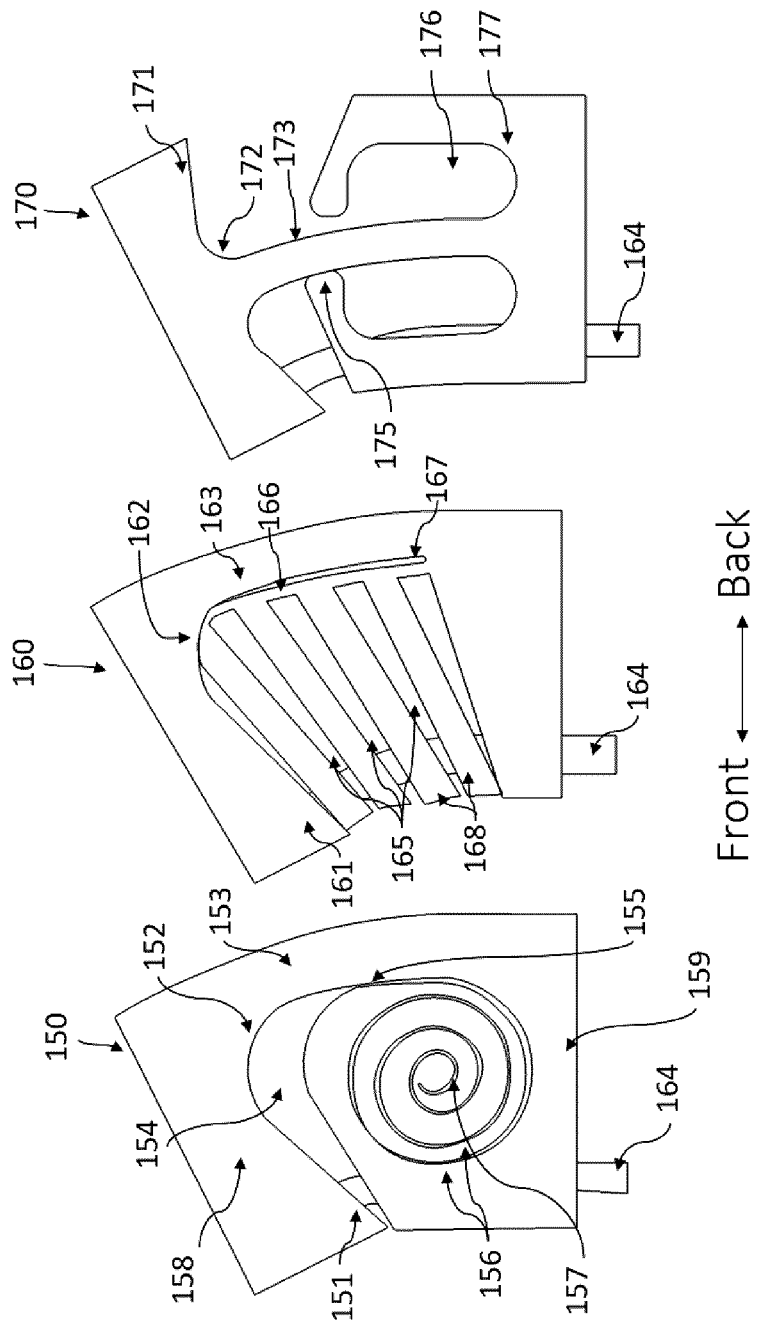
FIGS. 10A, 10B and 10C show three (3) alternative exemplary flexible articulate surgical tool notch topologies.

FIGS. 10A to 10C show some alternative exemplary flexible articulate surgical tool notch topologies. FIG. 10A shows a notch topology 150 which includes a circular cut-out 152 where the upper corner of transverse notch segment 151 terminates at the upper right corner of the notch and this provides for reduced strain concentration at this corner during bending of the upper section 158 with respect to the lower section 159. The notch segment 151 is tapered such that it will contact the lower portion of the tube just before the elastic strain limit of the tube material and geometry occurs. The flexible outer strip tube section 153 is a compliant section that may come into contact and slide or pivot about more rigid sections of the proximal tube section 159. These contact points are shown at 156 and 155 for example. These contact points will increase the blocking forces that the notch can support in a back to front direction. The elongated notch 157 is connected to the generally transvers notch 154 and follows an elongated curved path to reduce strain concentrations and to provide additional mobility to the compliant notch to provide a greater range of motion in bending. The elongated notch 157 is cut in a spiral or overlapping curved path pattern such that there is little resistance to rotational motion caused by the bending of the flexible outer strip tube section 153 but the opposing walls of the elongated notch 157 will come into contact and self-reinforce if loads are applied in the front or back directions. Notch topology 150 is different than notch topology 60 in that there are multiple contact points to self-reinforce and control the shape of the flexible outer strip tube section 153.

FIG. 10B also shows notch topology 160 which includes two compliant bending sections 163 and 166 that are arranged in parallel in the same notch. Compliant bending sections 163 will bend if an actuation load is applied along the actuation cable 164 or if an external load is applied in the back to front direction. When the compliant bending sections 163 displaces in a back to front direction, it will mechanically interfere with the second compliant bending sections 166 which will reinforce the notch and increase its stiffness in this loading direction. Notch topology 160 differs from 60 and 150 in that it includes multiple generally transverse sub-notch sections 165 that are sizes such that they will all be in contact with each other just before the elastic strain limit of the tube material and geometry occurs.

FIG. 10C additionally shows notch topology 170 which includes a symmetric profile with mechanical interference pins 175 that act to reinforce the shape of the flexible outer strip tube section 173 and to guide the shape that 173 undertakes while articulating. The spacing cavity 176 allows for off-center flexing of the flexible outer strip tube section 176 so that its range of motion is not inhibited by undesired mechanical interference. The corners 177 and 172 are curved to reduce strain concentrations.

Figure 12:
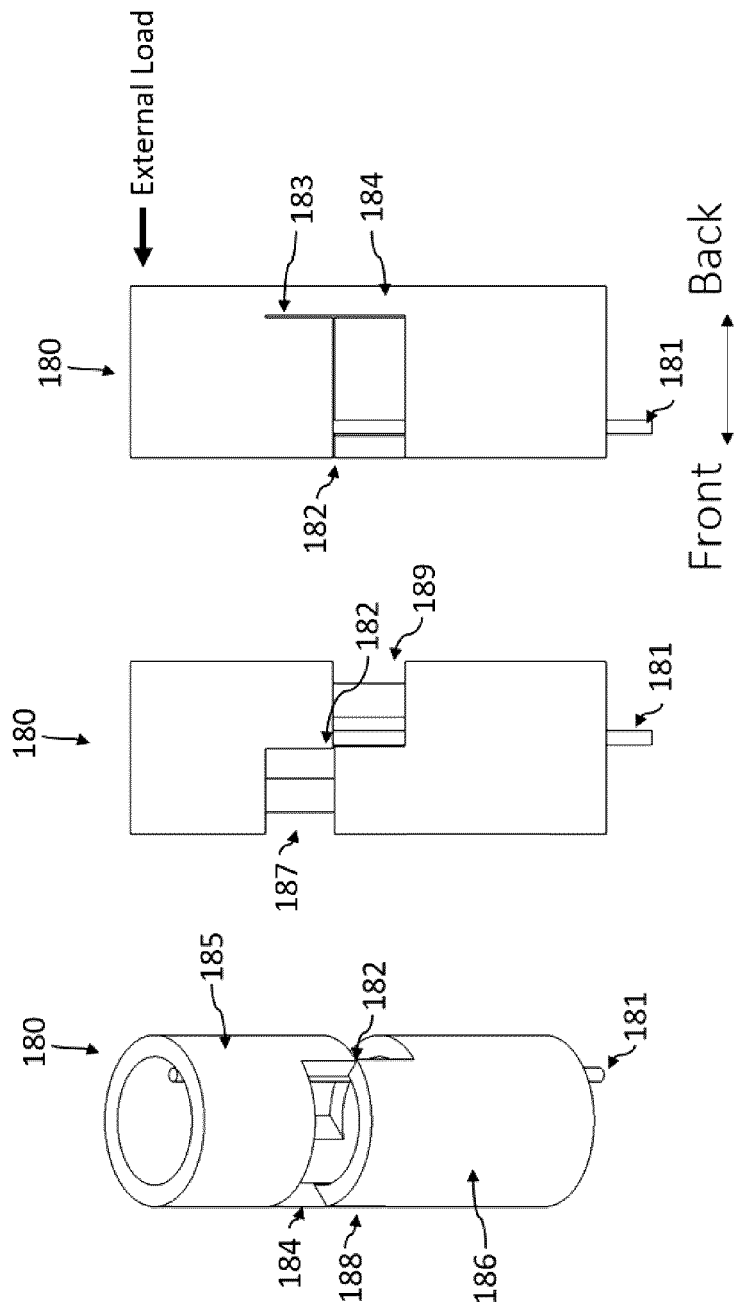
FIG. 12A shows a perspective view of an alternative exemplary flexible articulate surgical tool notch topology combined with a locking reinforcement design.
FIG. 12B shows a side elevation view of FIG. 12A where the reinforcement contact locking point 182 is visible.
FIG. 12C shows a side elevation view of FIG. 12A that is orthogonal to FIG. 12B. This view better illustrates the elongated notch segment 183.

FIG. 12A to 12C shows another exemplary flexible articulate surgical tool notch topology. FIG. 12A shows a notch topology 180 which includes an upper section 185 connected to a lower section 186 by means of a flexible outer strip tube section 184 that acts as a compliant section. This compliant section articulates by means of a flexible cable 181 that applies a bending and twisting force to the upper tube sections 185. The notch segment 187 is sized such that the bottom edge of the upper tube sections 185 will contact the lower portion of the tube 186 just before the elastic strain limit of the tube material and geometry occurs as the flexible cable 181 is articulated. The flexible outer strip tube section 184 is a compliant section that may come into contact and slide or pivot about more rigid sections of the tube lower section 186 for example when the elongated notch segment 188 closes upon itself during bending. The flexible outer strip tube section 184 is a compliant section that may come into contact and slide or pivot about more rigid sections of the tube upper section 185 for example when the elongated notch segment 183 closes upon itself during bending. These contact points will increase the blocking forces that the notch can support in a back to front direction.

FIG. 12B shows an alternate view of 12A. From this view, it can be appreciated that the generally transverse notch 187 is connected to the generally transverse notch 189 through a reinforcement contact locking point 182. When an external load is applied to the tube as shown in FIG. 12C, the upper tube section 185 is in contact with the lower tube section 186 through the point 182 such that the flexible outer strip tube section 184 is reinforced and prevented from bending. Conversely, when a bending force is applied to the upper tube section 185 by means of a flexible cable 181, the cable provides a downward and rotational force that unlocks the joint such that 185 and 186 no longer connect via 182 and the flexible outer strip tube section 184 is free to bend. While bending, the elongated notch 183 and 188 come into contact and self-reinforce to increase the stiffness of the notch through its range-of-motion. Notch topology 180 is different than notch topology 60 in that it combines mechanical reinforcement with mechanical closure and also with a locking mechanism to further increase the notch blocking forces in a defined configuration.

Figure 13:
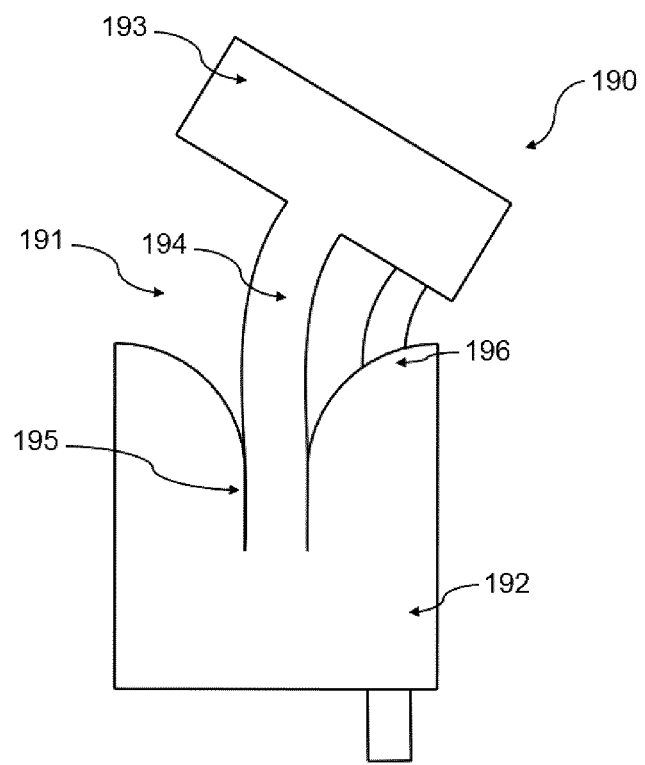
FIG. 13 show an alternative exemplary flexible articulate surgical tool notch topology for a symmetric design.

FIG. 13 shows another exemplary flexible articulate surgical tool notch topology 190 which includes an upper section 193 connected to a lower section 192 by means of a flexible strip tube section 194 that acts as a symmetric compliant section. This compliant section articulates by means of two flexible cables that apply bending forces on the upper tube section 193. The generally transverse notch segment 191 is sized such that the bottom edge of the upper tube section 193 will contact the lower portion of the tube 192 just before the elastic strain limit of the tube material and geometry occurs as the flexible cable is articulated. The flexible strip tube section 194 is a compliant section that may come into contact and slide or pivot about more rigid sections of the tube lower section 192 for example when the elongated notch segment 195 closes upon itself during bending. The top edge 196 of the bottom tube section 192 has a curved profile to guide the bending shape of the flexible strip tube section 194 as it articulates through its full range-of-motion.

A second means by which a flexible strip tube section is reinforced by other rigid sections of the joint involves having secondary sections attached proximal and distal to the flexible bending tube section. These secondary sections may be rigid or flexible and contact each-other to guide the bending of the flexible strip portion of the notch. Expressed in other terms, FIG. 18 uses two rolling surfaces to affect the shape of the compliant flexible bending strip region as it articulates.

FIGS. 18A and 18B show another exemplary flexible articulate surgical tool notch topology 220 which includes an upper section 221 connected to a lower section 222 by means of a flexible outer strip tube section 223 that acts as an asymmetric compliant section. Attached to and extending from the upper section 221 is a contact-aid section 224, and attached to and extending from the lower section 222 is another contact-aid section 225. Both of the contact-aid sections 224 and 225 include teeth or cogs 226 configured to mesh with each other. This compliant section articulates by means of one flexible cable 227 that applies a bending force on the upper tube section 221. The generally transverse notch segment 228, the space between the upper section 221 and the lower section 222, is sized such that the bottom edge of the upper tube section 221 will contact the lower portion of the tube 222 just before the elastic strain limit of the tube material and geometry occurs as the flexible cable is articulated. FIG. 18A shows the notch in an unactuated configuration and FIG. 18B shows the notch in an actuated configuration. The flexible outer strip tube section 223 is a compliant section that may come into contact and slide or pivot about more rigid sections of the contact-aid sections 224 or 225. Further, the contact-aid sections 224 and 225 may come into contact and slide, roll or pivot about each other during actuation as shown in FIG. 18B. The teeth or cogs 226 may come into contact and slide, roll or pivot about each other to guide the bending shape of the flexible outer strip tube section 223 and reinforce it as it articulates through its full range-of-motion.

The reinforcement of the flexible outer strip tube section by rigid sections demonstrated in FIG. 18 provides multiple benefits over a basic notch. First, the contact-aid sections 224 and 225 guide the bending of the flexible section such that the shape of the compliant bending region is more predictable. This feature simplifies the modelling of the notch's behavior and also increases the bending motion's repeatability. Second, the contact-aid sections 224 and 225 allow for larger achievable bending angles in an individual notch because taller notches are possible without risk of buckling while the sections 224 and 225 guide the notch's shape. This feature leads to more compact bending of the overall joint as fewer individual flexible notch sub-sections are required to achieve a desired bending angle. Third, the teeth or cogs 226 oppose forces that would cause the rolling surfaces to slip. Therefore, forces from the back of the joint will be transmitted into the teeth and the notch is stiffened. This increase in notch stiffness occurs throughout the notch's range of motion and without increasing strain concentrations.

The contact-aid sections 224 and 225 are aligned in parallel with the flexible outer strip tube section 223 and do not necessarily come into contact with the flexible outer strip tube section 223. Therefore, strain concentrations on the flexible outer strip tube section 223 during its bending will not be created by the contact-aids interacting with it directly. This elimination of strain concentrations from contact will improve the joint's life-cycle by reducing the max strains encountered during articulation. Additionally, arranging the contact-aid sections 224 and 225 parallel with the flexible outer strip tube section 223 provides an increased restoring force to return the notch to a straight position after use. Arranging the contact-aid sections 224 and 225 in parallel is different than, for example, the contact-aid shown in FIG. 5 which is arranged in a "3-point-bending" configuration. The parallel arrangement of the contact-aid sections 224 and 225 provide similar benefits without the need for the contact-aid to necessarily contact the flexible outer strip tube section 223. This feature eliminates any stress concentrations on the flexible outer strip tube section 223 caused by the contact-aid sections 224 and 225.

Figure 7:
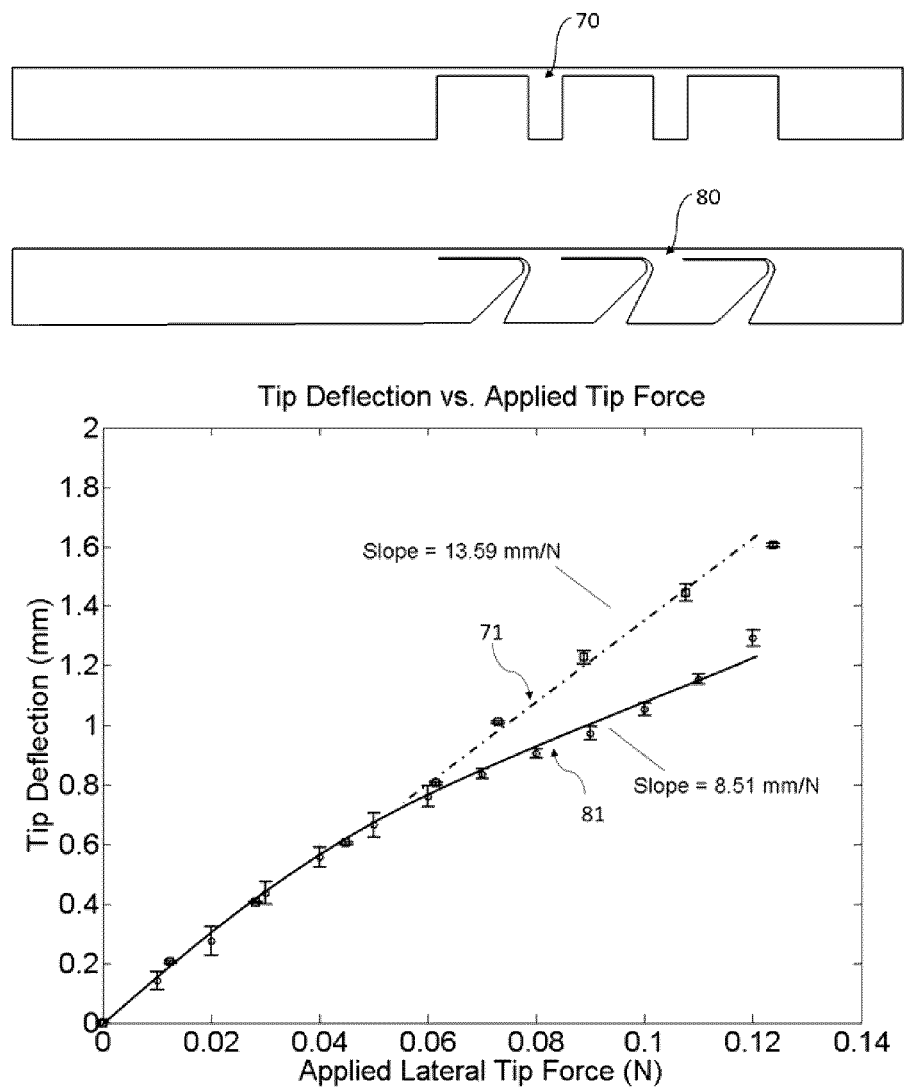
FIG. 7 shows two stiffness plots of joint tip displacement versus joint tip load where the joint tip load is based on the loading configuration as shown in FIG. 6. Here, the series indicated 81 corresponds to the joint design 80 and the series indicated 71 corresponds to the joint 70.

FIG. 7 shows that the stiffness of a joint topology with mechanical interference added in is more stiff than an equivalently sized joint without mechanical interference. The more horizontal the slope of the line, the stiffer the design. The two tools 70 and 80 being compared are cut from the same tube, and the maximum height and cut depth of the notches in both designs are the same. In the plot, the upper series 71 shows a square design's stiffness, corresponding to joint 70, compared to the lower series 81 showing the stiffness for a design of the present tool 80. These results clearly show that the notched joints of the present disclosure, shown in the lower tube 80, exhibit more desirable stiffness than the prior art notched joints 70.

Figure 8:
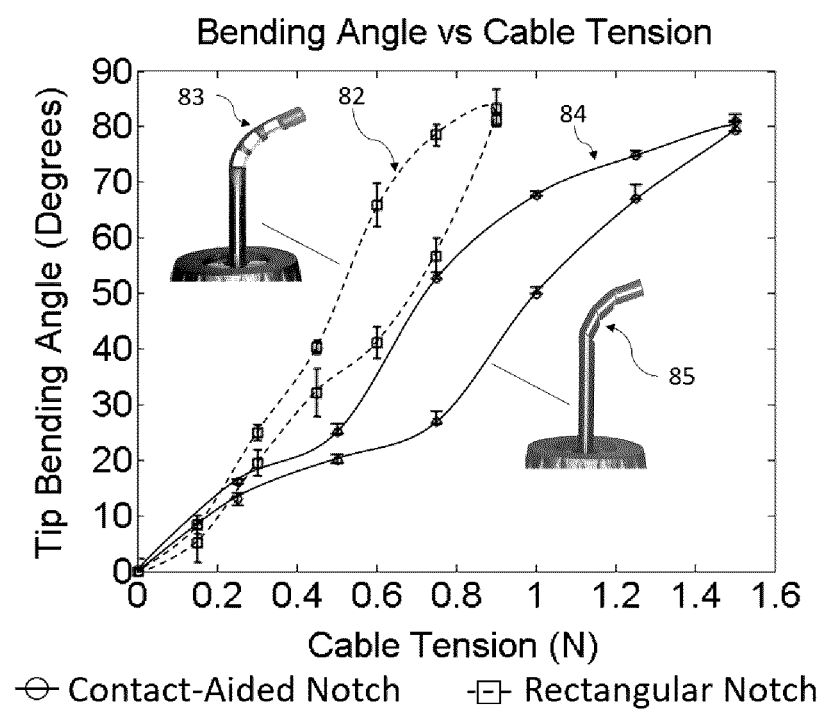
FIG. 8 shows a plot of joint bending angle as a function of the cable tension applied to articulate the tip of the joint. The plot has one series 82 corresponding to a joint constructed from the "basic" prior art notch design 83 (shown in the upper left of the FIG. 8) and another series 84 corresponding to a joint constructed from the present notch design 85 (shown in the bottom right of the FIG. 8). Both joints are capable of articulating through the same range-of-motion, and therefore, the modified notch with mechanical reinforcement and mechanical closure does not limit the maximum bending angle of the joint.

FIG. 8 depicts a plot of the cable tension (used to articulate the joints) and the bending angle of the tip of a joint made from "basic" rectangular notches 83 and the tip of a joint made from notches disclosed herein 85. Here we see that both joints are capable of reversibly bending (many 1000's of times) to approximately the same angle. This information is interpreted by observing that the top-right most point of the series 82 representing the joint 83 and the top-right most point of the series 84 representing the joint 85 are approximately at the same location in the Y-axis direction. The only difference is that the cable tension required for joint 85 is larger. In many cases, this trade-off is not significant from a design point of view because the cable, or other mechanism that provides the bending force to the tip, can be selected to support these higher loads, especially if the benefit is increased joint stiffness.

Figure 9:
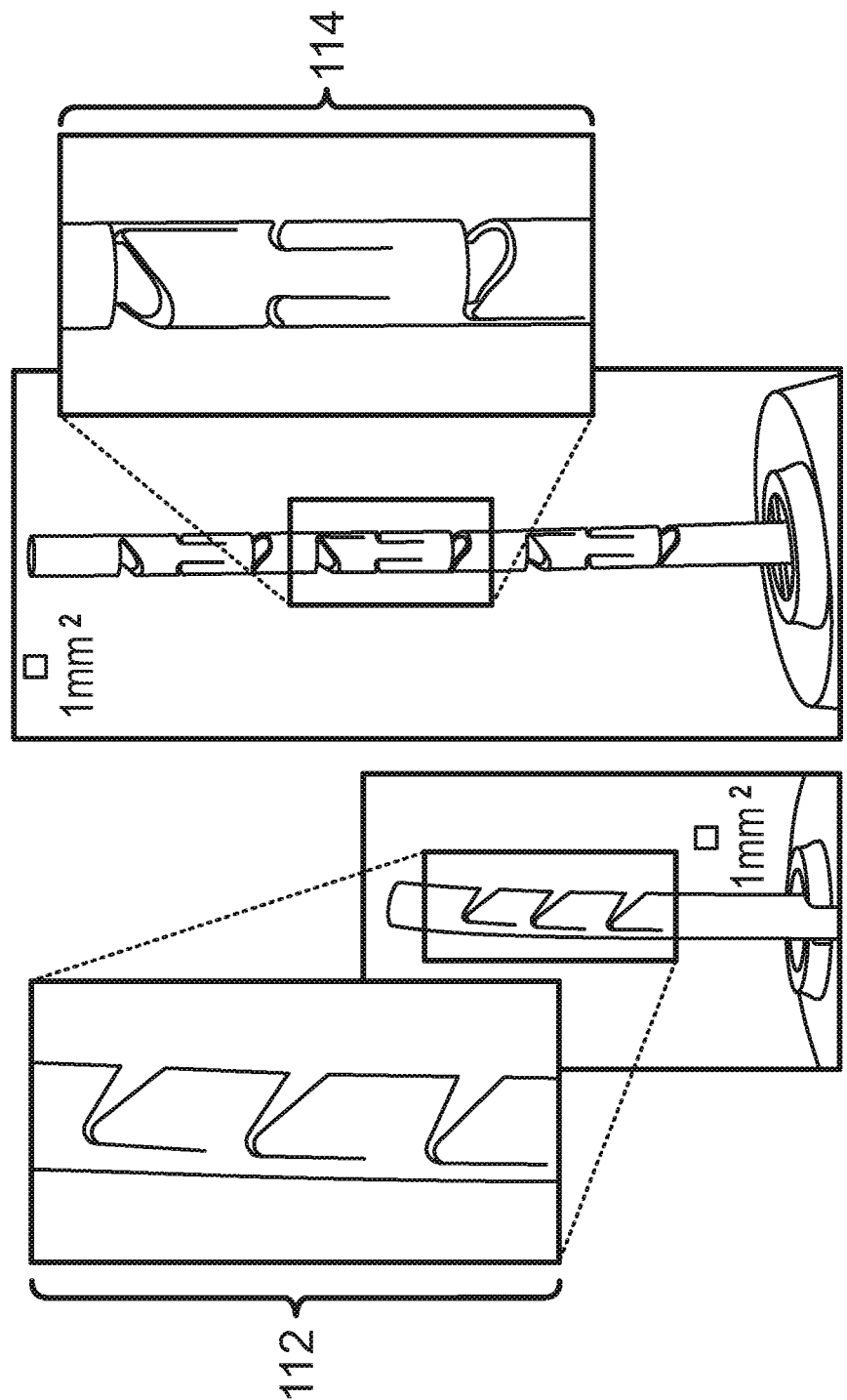
FIG. 9A depicts a joint disclosed herein comprised of three serially arranged modified notches with mechanical reinforcement and mechanical closure that articulates in one degree-of-freedom in a single direction.
FIG. 9B depicts a joint comprised of nine modified notches with mechanical reinforcement and mechanical closure that are helically arranged, along the long axis of the tube, and that articulate in two degrees-of-freedom in multiple directions.

FIG. 9A shows a side view of a part of a notched tube section with mechanical reinforcement and mechanical closure forming part of a flexible articulate surgical tool with several notched joints all aligned on one side of the tube to give an asymmetric arrangement of notches thereby giving a single bending direction to the tool. This configuration shows how the notches can be arranged in series to create a single degree-of-freedom joint.

FIG. 9B depicts a joint forming part of a flexible articulate surgical tool consisting of nine modified notches with mechanical reinforcement and mechanical closure to achieve multi-degree of freedom bending of the tube. Rotating the notches about the tube's axis allows for bending the tube in multiple planes. The embodiment shown in FIG. 9B involves offsetting each notch 120 degrees and arranging them helically, creating three primary bending directions. With the ability to actuate each of the primary bending directions independently, this arrangement of the joint allows the tube to bend in any direction. These figures indicate some ways in which the notches can be combined to produce more complex joints.

Figure 14:
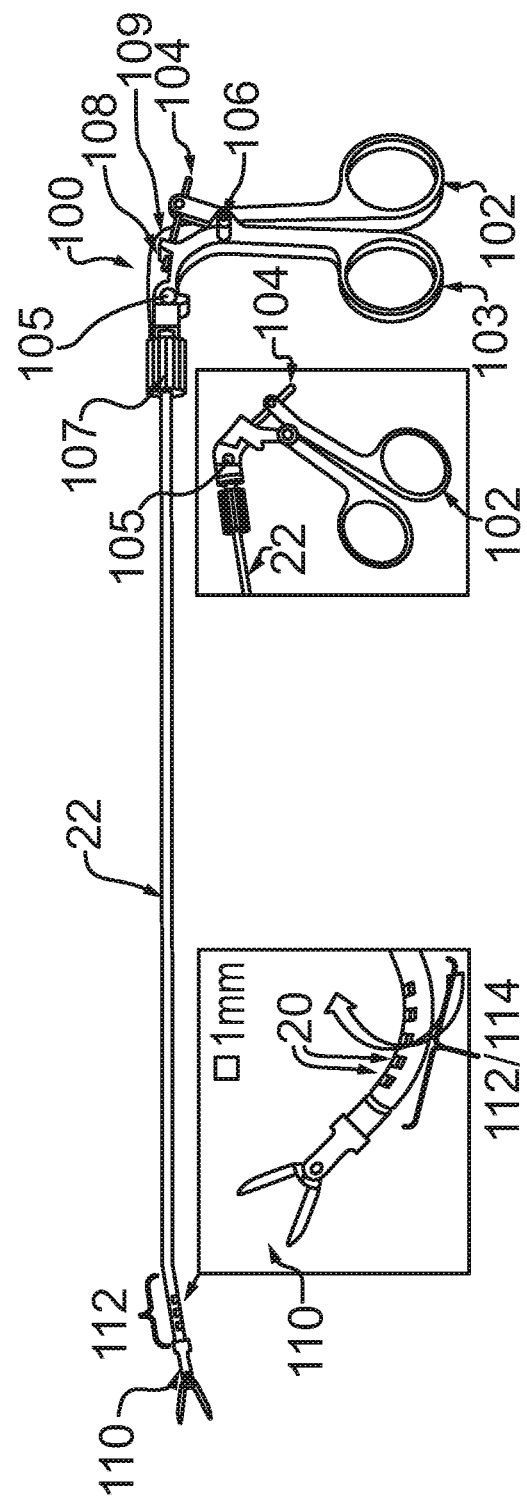
FIG. 14 shows an exemplary flexible articulate surgical tool 100 incorporating the notched tubes disclosed herein.

FIG. 14 shows an exemplary flexible articulate surgical tool 100 incorporating the notched tubes disclosed herein. This instrument configuration demonstrates one embodiment that may be used for neuroendoscopy applications. In this configuration, the tool is intended to be operated using one hand while being passed through the working channel of any commercially available or custom neuroendoscope.

The flexible surgical tool 100 includes a handle 102 configured in this case to be a ring handle design to which a proximal end of flexible wire 104 is connected. The definition of a ring handle is described in reference [12], which is incorporated herein by reference in its entirety. This ring handle 102 is constructed in this case from aluminum but could be constructed from any substitute metal (stainless steel, titanium, etc.) or plastic or other material. A distal end of the flexible wire 104 is connected to the surgical tool tip 110, also referred to as end-effector, which for example may be biopsy forceps. This flexible wire is routed within the instrument shaft 22 that is constructed from a flexible tube. In this case, the flexible tube 22 is constructed from nickel-titanium alloy (nitinol) but could be constructed from other substitute metals (stainless steel, titanium, etc.) or plastics. Tube section 112 located just before the tool tip 110, and attached distally to the instrument shaft 22, contains one or more joint sections 20. In this case, the tube section 122 is constructed from nickel-titanium alloy (nitinol) but could be constructed from any material with super-elastic properties, including polymers. The instrument shaft 22 is connected to the instrument handle 103 by a collet mechanism 107. The ring handle 102 is operably connected to the biopsy forceps tool tip 110 via the flexible wires 104 within the shaft 22 such that actuation of the ring handle, pivoting it about the joint 106, results in opening and closing of the end-effector 110.

A proximal end of flexible cable 109 is fixed to a part of the instrument handle 103 via a clamping mechanism 103 that is fixed using set screws in this case. This connection between 109 and 103 could be achieved by other means such as laser welding, or a different variation of fixation or mechanical clamping. A distal end of the flexible cable 109 is fixed to the distal end of notched joint instrument shaft 112, proximal to the end-effector 110. The flexible cable 109 routes within the flexible tube 22. To actuate the notched joint section 112, rotation about the joint 105 will apply tension to the flexible cable 109 and cause the joints 112 to close.

FIG. 14 shows the surgical tool employing biopsy forceps for removing tissue, however it will be appreciated that the surgical tool may be any tool requiring a flexible jointed section for providing the same type of stiffness as tool 100 is provided with. For example, the end-effector could be replaced with biopsy forceps, ventriculostomy forceps, grasping forceps, angled or curved scissors, bipolar forceps, guillotine knife, scalpel, bipolar coagulation electrode, burr or drill bits, ultrasonic aspirator or scalpel or laser ablation probes. The tip could also be fitted with a mechanism to deploy drugs/medications, stents, or probes or electrodes. It will be appreciated that the surgical tool could be used to position diagnostic devices for laser scanning or ultrasound. Some alternative embodiments could include the use of this technology in teleoperated surgical robotic manipulators, for example, on the tip or embedded within the body of a concentric tube robotic platform. The technology could also be attached to the tip or body of an endovascular catheter for the purposes of targeted drug delivery, stent deployment or laser ablation therapy.

Figure 15:
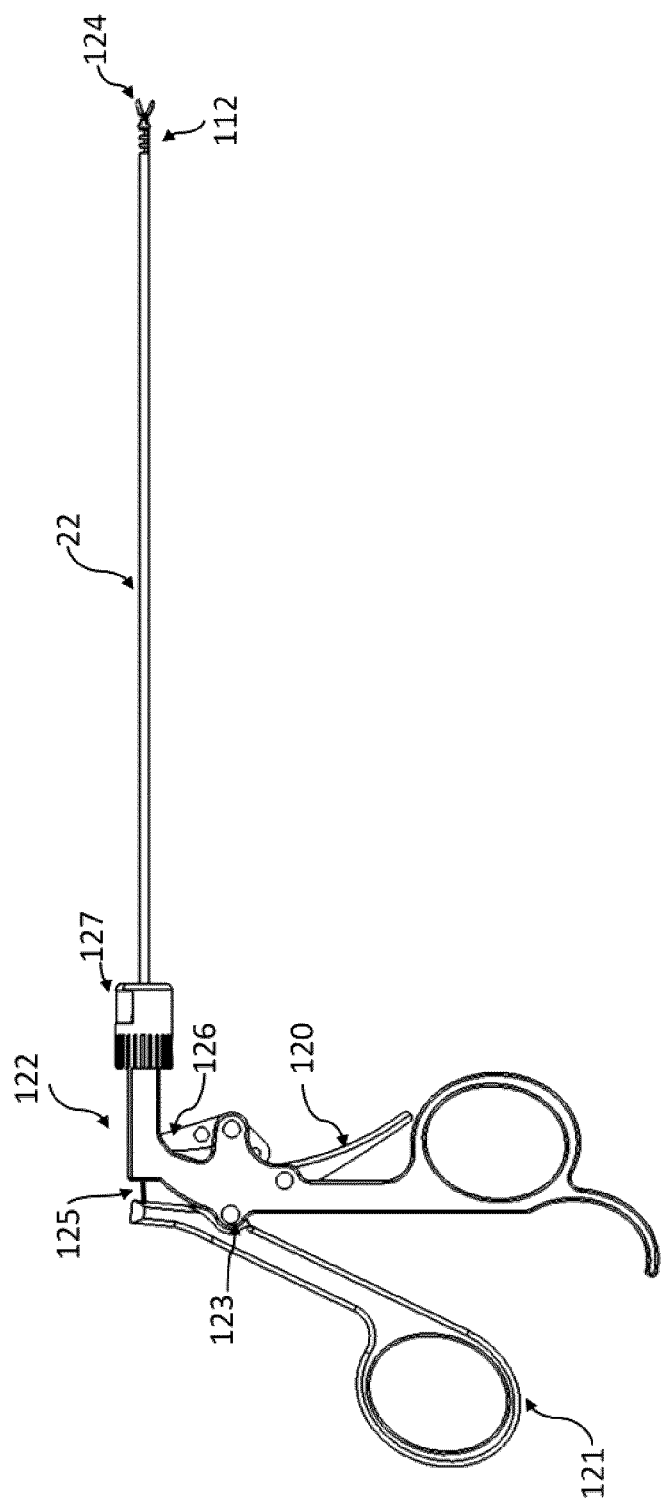
FIG. 15 shows an alternative ring handle configuration with a trigger mechanism 126 and a similar form to the handle design shown in FIG. 14.

FIG. 15 shows an alternative exemplary flexible articulate surgical tool 122 incorporating the notched tubes disclosed herein. This design is configured similar to 100 in FIG. 14. In the case of 122, the ring handle 121 is attached to the proximal end of a flexible cable 125 whose distal end is attached to the notched joint instrument shaft 112. The ring handle 121 is used to articulate the notch joint instrument shaft as the ring handle is pivoted about the joint 123. Through this motion, tension is applied to the cable 125 causing the notch joint 112 to bend. The trigger mechanism 120 is used to actuate the end-effector 124, which in this case is shown to be scissors. The trigger 120 is connected to a lever mechanism 126 which is connected to a proximal end of flexible wires within the shaft 22. The distal end of flexible wires connect to the end-effector scissors 124 such that articulating the trigger mechanism 120, also articulates 126 which applies tension and compression to the flexible wires to open close and open the scissors 124.

Figure 16:
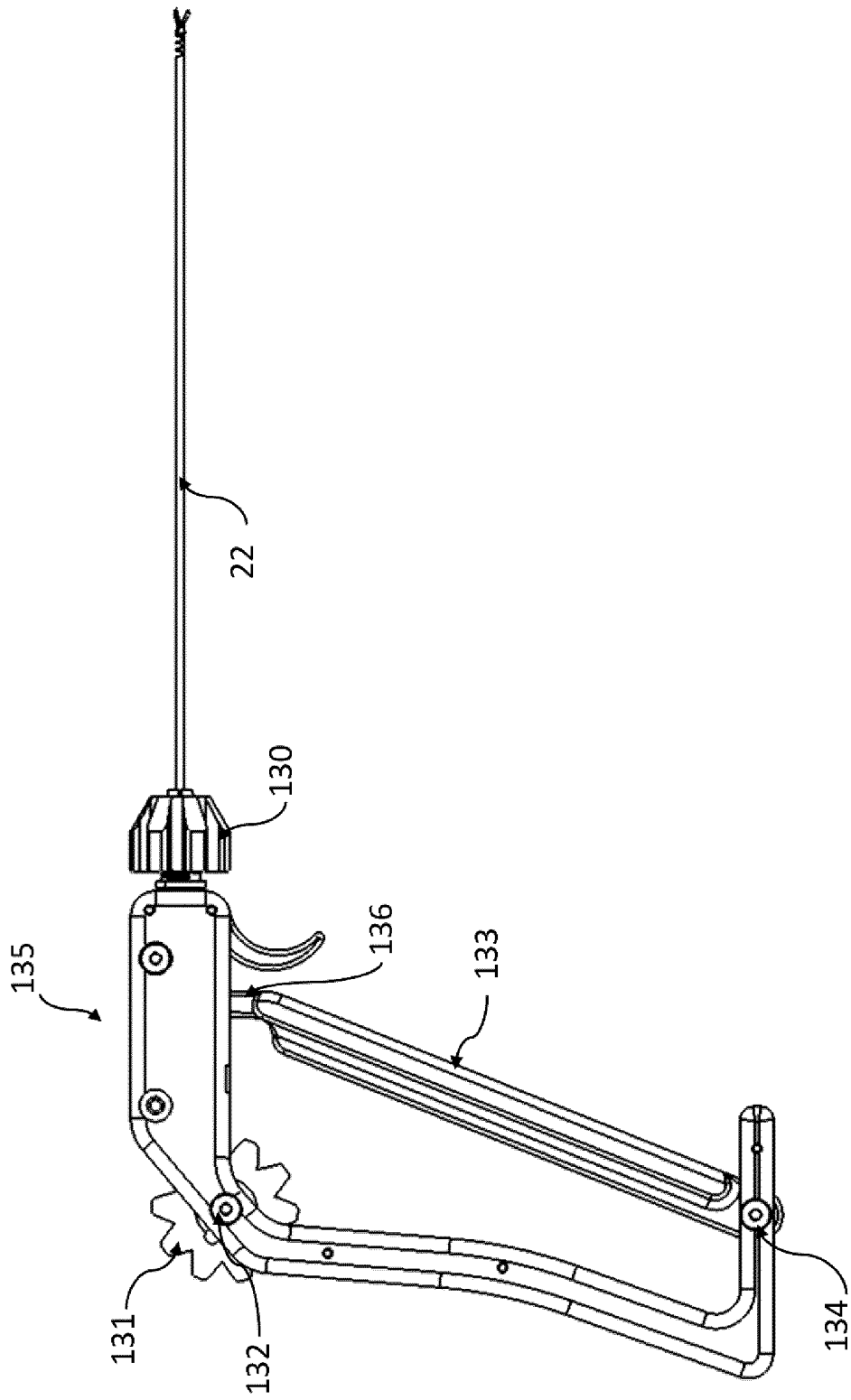
FIG. 16 shows an alternative handle design 135 where a thumb wheel 131, which rotates around a joint 132, is connected to a proximal end of a flexible cable.
Figure 17:
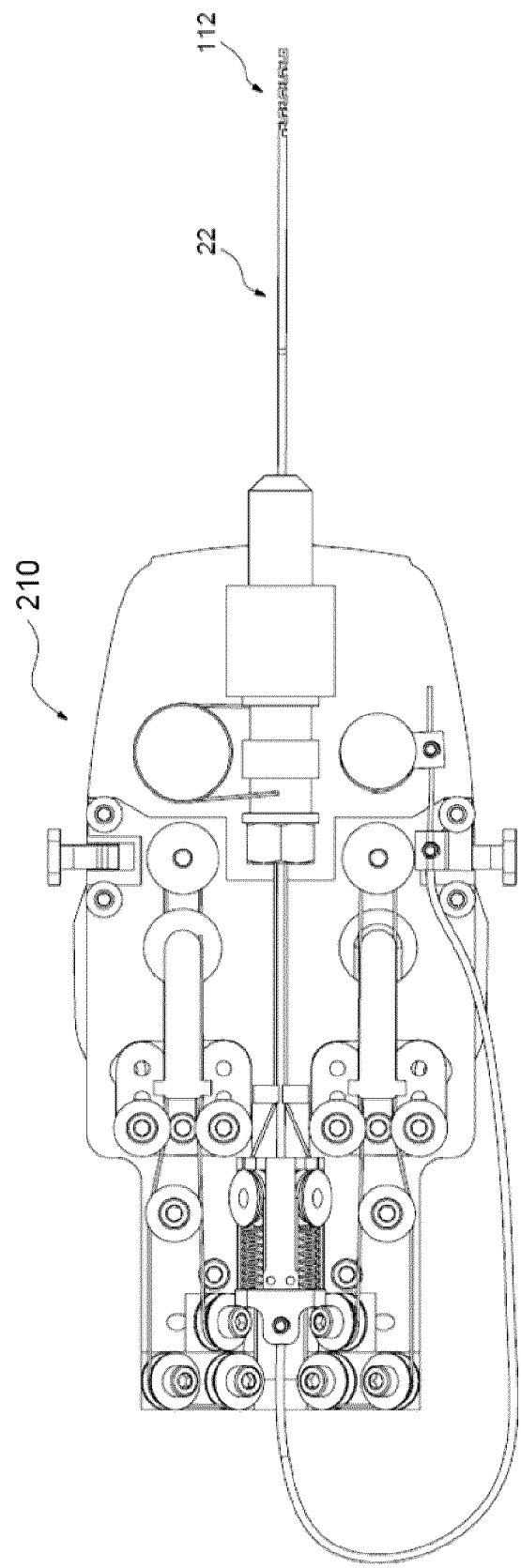
FIG. 17 depicts the notched tube designs on a robotic device. At the base of the device 210, proximal to the tube shaft 22, a series of mechanisms are driven to control the bending of the notched tube section 112. Typically, the robotic devices control bending of the notched tube joint in multiple directions.

FIG. 16 shows an alternative handle design 135 where a thumb wheel 131, which rotates around a joint 132, is connected to a proximal end of flexible cable. The distal end of the flexible cable is connected to the notched joint 112, such that when the thumb wheel 131 is spun, tension is applied to the flexible cable and the joint 112 is actuated and bends. A spring-loaded trigger mechanism 133 is configured such that is pivots about the joint 134. The distal tip of the trigger mechanism 136 is connected to a proximal end of flexible wire. The distal end of flexible wire is connected to an end-effector 110 such that when the trigger 133 is articulated, the end-effector opens and closes. A finger wheel 130 is rigidly connected to the flexible shaft 22 and the finger wheel 130 is connected to the instrument 135 but free to rotate about the axis collinear with the shaft 22. The finger wheel 130 has a dual purpose in acting as a collet to clamp the flexible tube 22 in-place, similar to 107, and also to act to control an additional degree-of-freedom. It will be appreciated that the finger wheel may be spun to rotate the flexible shaft 22 and thereby change the orientation of the end-effector 110.

FIGS. 19A to 19C show an alternative exemplary flexible articulate surgical tool 230 incorporating the notched tubes disclosed herein. The flexible surgical tool 230 includes a handle 231, constructed in this case from aluminum but could be constructed from any substitute metal (stainless steel, titanium, etc.) or plastic or other material. The flexible surgical tool 230 also includes an instrument shaft 232 that is constructed from a flexible tube. In this case, the flexible tube 232 is constructed from nickel-titanium alloy (nitinol) but could be constructed from other substitute metals (stainless steel, titanium, etc.) or plastics. The instrument shaft 232 in this case has two different outer diameters, but could be constructed from one or multiple diameters by attaching multiple tubes together. The instrument shaft 232 is attached to a flexible region of the shaft 233 that in this case consists of three compliant notched joints, but could consist of any number of notches in any of the variations described herein. The shape and profile of these compliant notches is best appreciated in FIG. 19B. In this case, the flexible region 233 is constructed from nickel-titanium alloy (nitinol) but could be constructed from any material with super-elastic properties, including polymers. A distal end of flexible cable 237 is fixed to a part of the instrument tip 236. The flexible cable 237 is routed within the lumen of the instrument shaft 232. At the distal end of the instrument shaft 233 a surgical tool tip 234, also referred to as end-effector, is connected, which for this example are scissors. These end-effectors are best seen in FIG. 19A. A distal end of the flexible wire 235 is connected to the surgical tool tip for actuation 234 where this flexible wire 235 is routed within the lumen of the instrument shaft 232.

The instrument shaft 232 is connected to the instrument handle 231 by a collet mechanism 238. The handle 231 is operably connected to the scissor end-effector tool tip 234 via the flexible wires 235 within the shaft 232 such that translating the middle ring handle 239 along the prismatic joint 240 results in opening and closing of the end-effector 234. The prismatic joint is constructed from a concentric assembly of the ring handle 239 and the handle gimbal 243. The alignment of the prismatic joint is maintained by a slot 245 and an alignment pin 246. A compression spring 247 is used to create a restoring force and maintain the prismatic joint in a fully extended resting position. A proximal end of flexible wire 235 is fixed to a part of the instrument ring handle 239 via a clamping mechanism 241 that is fixed using set screws in this case. This connection between 235 and 239 could be achieved by other means such as laser welding, or a different variation of fixation or mechanical clamping. The assembly of the ring handle 239 and the handle gimbal 243 with the compression spring 247 is shown in the exploded-view in FIG. 19C.

The handle 231 is operably connected to the flexible joint region 233 via the flexible cable 237 within the shaft 232 such that pivoting the ring handle 239 about the pin joint 242 results in a pitch motion of the notched-tube compliant joint instrument shaft 233. The pivoting motion of 239 will apply tension to the flexible cable 237 and cause the joints 233 to close. A proximal end of flexible cable 237 is fixed to a part of the handle gimbal 243 via a clamping mechanism 244 that is fixed using set screws in this case. This connection between 237 and 243 could be achieved by other means such as laser welding, or a different variation of fixation or mechanical clamping.

FIGS. 19A and 19B shows the surgical tool employing scissors for the end-effector, however similar to all of the handle presented herein, it will be appreciated that the end-effector may be any tool requiring a flexible jointed section similar to FIG. 14.

The foregoing description of the preferred embodiments of the disclosure has been presented to illustrate the principles of the disclosure and not to limit the disclosure to the particular embodiment illustrated. It is intended that the scope of the disclosure be defined by all of the embodiments encompassed within the following claims and their equivalents.

REFERENCES

1] P. J. Swaney, P. A. York, H. B. Gilbert, J. Burgner-Kahrs, and R. J. Webster III, "Design, Fabrication, and Testing of a Needle-sized Wrist for Surgical Instruments," *ASME J. Med. Devices*, no. c, 2016.

[2] H. Fischer, B. Vogel, W. Pfleging, and H. Besser, "Flexible distal tip made of nitinol (NiTi) for a steerable endoscopic camera system," *Mater. Sci. Eng. A*, vol. 273-275, pp. 780-783, 1999.

[3] J. Peirs, H. Van Brussel, D. Reynaerts, and G. De Gersem, "A Flexible Distal Tip with Two Degrees of Freedom for Enhanced Dexterity in Endoscopic Robot Surgery," in *The 13th Micromechanics Europe Workshop*, 2002, pp. 271-274.

[4] Y. Haga, Y. Muyari, S. Goto, T. Matsunaga, and M. Esashi, "Development of Minimally Invasive Medical Tools Using Laser Processing on Cylindrical Substrates," *Electr. Eng. Japan*, vol. 176, no. 1, pp. 65-74, 2011.

[5] M. D. M. Kutzer, S. M. Segreti, C. Y. Brown, R. H. Taylor, S. C. Mears, and M. Armand, "Design of a New Cable-Driven Manipulator with a Large Open Lumen: Preliminary Applications in the Minimally-Invasive Removal of Osteolysis," in *IEEE International Conference on Robotics and Automation*, 2011, pp. 2913-2920.

[6] S. C. Ryu, P. Renaud, R. J. Black, B. L. Daniel, and M. R. Cutkosky, "Feasibility Study of an Optically Actuated MR-compatible Active Needle," in *IEEE International Conference on Intelligent Robots and Systems*, 2011, pp. 2564-2569.

[7] D. Wei, Y. Wenlong, H. Dawei, and D. Zhijiang, "Modeling of Flexible Arm with Triangular Notches for Applications in Single Port Access Abdominal Surgery," in *IEEE International Conference on Robotics and Biomimetics*, 2012, pp. 588-593.

[8] J. A. Bell, C. E. Saikus, K. Ratnayaka, V. Wu, M. Sonmez, A. Z. Faranesh, J. H. Colyer, R. J. Lederman, and O. Kocaturk, "A Deflectable Guiding Catheter for Real-Time MRI-Guided Interventions," *J. Magn. Reson. Imaging*, vol. 35, no. 4, pp. 908-915, 2012.

[9] J. Liu, B. Hall, M. Frecker, and E. W. Reutzel, "Compliant articulation structure using superelastic NiTiNOL," *Smart Mater. Struct.*, vol. 22, no. 9, 2013.

[10] N. Lobontiu, M. Cullin, T. Petersen, J. a Alcazar, and S. Member, "Planar Compliances of Symmetric Notch Flexure Hinges: The Right Circularly Corner-Filleted Parabolic Design," vol. 11, no. 1, pp. 169-176, 2014.

[11] P. A. York, P. J. Swaney, H. B. Gilbert, and R. J. Webster III, "A Wrist for Needle-Sized Surgical Robots," in *IEEE International Conference on Robotics and Automation*, 2015, pp. 1776-1781.

[12] U. Matern, G. Kuttler, C. Giebmeyer, P. Waller, and M. Faist, "Ergonomic aspects of five different types of laparoscopic instrument handles under dynamic conditions with respect to specific laparoscopic tasks: an electromyographic-based study.," *Surg. Endosc.*, vol. 18, no. 8, pp. 1231-41, 2004.

Therefore what is claimed is:

1. A flexible elongate shaft assembly, comprising:
    an elongate flexible shaft having at least one joint built into the elongate flexible shaft, the at least one joint comprised of at least one notch, with each notch having an internal section contact-aided compliant notch topology within each notch configured to cause the internal section of each notch, upon bending in which each notch is bending when each notch's internal section contact-aided compliant notch topology is deforming and the strain on the material of the contact-aided compliant notch topology is changing, to
    mechanically interfere with itself and self-reinforce prior to each notch being fully bent resulting in an increase in stiffness of each notch prior to being fully bent and to prevent buckling and plastic deformation of the elongate flexible shaft, and assume a predetermined and designed bending shape of the at least one joint and hence the elongate flexible shaft.

2. The flexible elongate shaft assembly according to claim 1, wherein the elongate flexible shaft is an elongated tube having a longitudinal axis, and wherein the contact-aided compliant notch topology comprises a generally transverse notch segment extending from a first side of the elongated tube towards an opposed second side of the elongated tube and terminating at a predetermined termination position adjacent to, and spaced from, the second side of the elongated tube, the generally transverse notch segment dividing the elongated tube into a proximal tube section located on one side of the generally transverse notch segment and a distal tube section located on the other side of the generally transverse notch segment, an elongated notch segment extending from the generally transverse notch segment at the predetermined termination position in a direction generally parallel to the longitudinal axis to define a flexible outer strip tube section along the opposed second side of the elongated tube connecting the proximal and distal tube sections, and wherein the elongated notch segment has a preselected width such that upon movement of the distal tube section, relative to the proximal tube section, in a direction from the second side towards the first side, an inner surface of the flexible outer strip tube section adjacent to the elongated notch segment comes into physical contact with an internal section of the proximal tube section adjacent to both the predetermined termination position and the elongated notch segment causing the at least one notch to mechanically interfere with itself and self-reinforce throughout the range-of-motion of the at least one notch.

3. The flexible elongate shaft assembly according to claim 2, wherein the preselected width of the elongated notch segment is selected to give a predetermined amount of movement of the distal tube section with respect to the proximal tube section prior to the inner surface of the flexible outer strip tube section adjacent to the elongated notch segment coming into physical contact with the internal section of the proximal tube section.

4. The flexible elongate shaft assembly according to claim 3, wherein the preselected width of the elongated notch segment is variable such that at a transition zone between the generally transverse notch segment and the elongated notch segment, the width of the elongated notch segment, defined as the distance between the inner surface of the flexible outer strip tube section adjacent to the elongated notch segment and the internal section of the proximal tube section, varies between an initial width to a final width, where the initial width is greater than the final width.

5. The flexible elongate shaft assembly according to claim 2, wherein the generally transverse notch segment extending from the first side of the elongated tube towards the opposed second side of the elongated tube is tapered from a first opening size at the first side of the elongated tube down to a second opening size at the predetermined termination position such that the first opening size is greater than the second opening size, and wherein the first opening size is selected such that an end section of a distal tube section located on the first side of the elongated tube adjacent to the tapered notch segment and an end section of a proximal tube section located on the first side of the elongated tube adjacent to the tapered notch segment come into contact only at the end of a range-of-motion of each notch such that when the end section of the distal tube section located on the first side of the elongated tube adjacent to the tapered notch segment and the end section of the proximal tube section located on the first side of the elongated tube adjacent to the tapered notch segment come into contact each notch cannot bend anymore, and wherein the first opening size is selected to ensure contact occurs just before a flexible part of each notch reaches any plastic deformation.

6. The flexible elongate shaft assembly according to claim 2, wherein the at least one joint is a plurality of joints spaced along the elongated tube.

7. The flexible elongate shaft assembly according to claim 6, wherein the plurality of joints spaced along the elongated tube are aligned collinearly along the elongated tube such that the elongated tube actuates in a single plane upon application of a force.

8. The flexible elongate shaft assembly according to claim 6, wherein the plurality of joints spaced along the elongated tube are aligned in a non collinear configuration around the elongated tube such that the elongated tube actuates in a plurality of planes upon application of a force.

9. The flexible elongate shaft assembly according to claim 6, wherein the plurality of joints spaced along the elongated tube are aligned in a helical configuration around the elongated tube such that the elongated tube actuates in a plurality of planes upon application of a force.

10. The flexible elongate shaft assembly according to claim 9, wherein the plurality of joints are spaced in a predetermined helical configuration around the elongated tube at a preselected angle spiral spacing with respect to each other.

11. The flexible elongate shaft assembly according to claim 10, wherein the preselected angle spiral spacing is 120 degree spiral spacing.

12. The flexible elongate shaft assembly according to claim 10, wherein the preselected angle spiral spacing is 90 degree spiral spacing.

13. The flexible elongate shaft assembly according to claim 2, wherein including a cut-out located in the distal tube section located at an end of the generally transverse notch segment adjacent to the predetermined termination position configured to provide reduced strain concentration during bending of the flexible outer strip tube section.

14. The flexible elongate shaft assembly according to claim 2, wherein the elongated notch segment includes an inner surface and an outer surface, and wherein the elongated notch segment is extended into the internal section of the proximal tube section in a spiral configuration such that multiple points of mechanical interference contact occur between the inner surface and outer surface of the elongated notch segment causing increased stiffness throughout the notch's range-of-motion; where the inner surface of the elongated notch segment is continuous with the inner surface of the flexible outer strip tube section and the outer surface of the elongated notch segment is continuous with the internal section of the proximal tube section adjacent to both the predetermined termination position and the elongated notch segment.

15. The flexible elongate shaft assembly according to claim 2, wherein the internal section of the proximal tube section has a least one additional slit included in the notch topology where the at least one additional slit is generally parallel with the generally transverse notch segment, and the length of the at least one additional slit is such that it approaches but does not connect with the elongated notch segment, and a width of the at least one additional slit is such that two edges come into contact throughout the at least one notch's range-of-motion to increase the stiffness of the at least one notch, and wherein the two edges of the at least one additional slit include a distal edge closer to the distal tube section and a proximal edge closer to the proximal tube section.

16. The flexible elongate shaft assembly according to claim 2, wherein the notch topology further comprises a generally axial notch segment, wherein said generally axial notch segment is generally parallel with the flexible outer strip tube section and has a predefined length and width that extend into the internal section of the proximal tube section, and wherein the elongated notch segment is a region between an edge of the flexile outer strip tube section and a section of the internal section of the proximal tube section that is generally parallel with the generally transverse notch segment and encloses the generally axial notch segment to provide mechanical reinforcement of the at least one notch by contacting the flexible outer strip tube section throughout the at least one notch's range of motion.

17. The flexible elongate shaft assembly according to claim 16, wherein two notch topologies are arranged in a mirrored configuration, sharing a single flexible tube section set an equal distance from the first side of the elongated tube towards the opposed second side of the elongated tube, allowing the at least one notch to bend in directions either towards the first side of the elongated tube or the second side of the elongated tube while having mechanical reinforcement throughout the range of motion of the at least one notch.

18. The flexible elongate shaft assembly according to claim 2, wherein a separate rigid tube member is assembled concentrically with the elongate flexible shaft such that the separate rigid tube member is in a region between the distal tube section and proximal tube section of the generally transverse notch segment of the at least one notch and a new elongated notch segment is the region between the flexible outer strip tube section and the separate rigid tube member.

19. The flexible elongate shaft assembly according to claim 18, wherein the new elongated notch segment has a preselected width such that upon movement of the distal tube section, relative to the proximal tube section and the separate rigid tube member, in a direction from the second side towards the first side, an inner surface of the flexible outer strip tube section adjacent to the elongated notch segment comes into physical contact with an internal section of the separate rigid tube member adjacent to both the predetermined termination position and the elongated notch segment causing the at least one notch to mechanically interfere with the separate rigid tube member and self-reinforce throughout the notch's range of motion.

20. The flexible elongate shaft assembly according to claim 2, wherein the generally transverse notch segment is configured to be at a proximal portion of the at least one notch, and the elongated notch segment is configured to be at a distal portion of the at least one notch such that contact-aid occurs between an internal section of the distal tube section and the flexible outer strip tube section.

21. The flexible elongate shaft assembly according to claim 1, wherein the elongate flexible shaft is an elongated tube having a longitudinal axis, and wherein the contact-aided compliant notch topology comprises a generally transverse notch segment extending from a first side of the elongated tube towards an opposed second side of the elongated tube and terminating at a predetermined termination position adjacent to, and spaced from, the second side of the elongated tube, the generally transverse notch segment dividing the elongated tube into a proximal tube section located on one side of the generally transverse notch segment and a distal tube section located on the other side of the generally transverse notch segment and being connected by a flexible outer strip tube section along the opposed second side of the elongated tube connecting the proximal and distal tube sections, the distal tube section including a first toothed contact-aid section depending therefrom and extending into the generally transverse notch segment, and the proximal tube section including a second toothed contact-aid section depending therefrom and extending into the generally transverse notch segment with the first and second toothed contact-aid sections configured to mesh together such that upon movement of the distal tube section, relative to the proximal tube section, in a direction from a second side towards a first side, the first and second toothed contact-aid sections come into physical contact and mesh with each other causing the at least one notch to mechanically interfere with itself and self-reinforce.

22. The flexible elongate shaft assembly according to claim 21, wherein the at least one joint is a plurality of joints spaced along the elongated tube.

23. The flexible elongate shaft assembly according to claim 22, wherein the plurality of joints spaced along the elongated tube are aligned collinearly along the elongated tube such that the elongated tube actuates in a single plane upon application of a force.

24. The flexible elongate shaft assembly according to claim 22, wherein the plurality of joints spaced along the elongated tube are aligned in a non collinear configuration around the elongated tube such that the elongated tube actuates in a plurality of planes upon application of a force.

25. The flexible elongate shaft assembly according to claim 22, wherein the plurality of joints spaced along the elongated tube are aligned in a helical configuration around the elongated tube such that the elongated tube actuates in a plurality of planes upon application of a force.

26. The flexible elongate shaft assembly according to claim 22, wherein the plurality of joints are spaced in a predetermined helical configuration around the elongated tube at a preselected angle spiral spacing with respect to each other.

27. The flexible elongate shaft assembly according to claim 26, wherein the preselected angle spiral spacing is 120 degree spiral spacing.

28. The flexible elongate shaft assembly according to claim 26, wherein the preselected angle spiral spacing is 90 degree spiral spacing.

29. The flexible elongate shaft assembly according to claim 1, incorporated into a surgical tool, wherein a proximal end section of the elongate flexible shaft is operably connected to a clinician operated handle, and wherein a distal end section of the elongate flexible shaft is operably connected to the surgical tool, including a first cable connected to a most distal joint adjacent to the surgical tool and connected to the clinician operated handle and all intervening joints between the most distal joint and the clinician operated handle with the connection between the first cable and the clinician operated handle configured to allow a clinician to activate the first cable to induce joint actuation of the flexible elongate shaft assembly to a degree determined by the clinician, and including a second cable connected between the surgical tool and the clinician operated handle to allow the clinician to operate the surgical tool.

30. The flexible elongate shaft assembly connected to a clinician operated handle according to claim 29, wherein the handle is comprised of three assemblies, where a first assembly rigidly holds the elongate flexible shaft and is connected to a second assembly by a first pin joint and the activation of the first cable to induce joint actuation is achieved by pivoting the second assembly with respect to the first assembly about the first pin joint, and including a third assembly connected to the second assembly by a second pin joint and pivoting of the third assembly with respect to the second assembly about the second pin joint allows a clinician to push and pull the second cable and to open and close the surgical tool at a tip of the elongate flexible shaft.

31. The flexible elongate shaft assembly connected to a clinician operated handle according to claim 29, wherein the handle is comprised of three assemblies, wherein a first assembly rigidly holds the elongate flexible shaft and is connected to a second assembly by a first pin joint and activation of the first cable to induce joint actuation is achieved by pivoting the second assembly with respect to the first assembly about the first pin joint, and wherein a third assembly having a trigger mechanism is connected to the second assembly by a second pin joint and activation of the trigger mechanism of the third assembly allows a clinician to push and pull the second cable and to open and close the surgical tool at a tip of the elongate flexible shaft.

32. The flexible elongate shaft assembly connected to a clinician operated handle according to claim 29, wherein the handle is comprised of four assemblies, where a first assembly rigidly holds the elongate flexible shaft and is connected to a second assembly such that rotation of the first assembly about a long axis of the elongate flexible shaft allows rotation of the elongate flexible shaft with respect to the handle, and including a third assembly comprised of a wheel mechanism that is connected to the second assembly by a first pin joint and the activation of the first cable to induce joint actuation is achieved by rolling the third assembly with respect to the second assembly about the first pin joint, and further including a fourth assembly which comprised of a trigger mechanism is connected to the second assembly by a second pin joint, and wherein activation of the trigger mechanism of the fourth assembly allows a clinician to push and pull the second cable and to open and close the surgical tool at a tip of the elongate flexible shaft.

33. The flexible elongate shaft assembly connected to a clinician operated handle according to claim 29, wherein the handle is comprised of four assemblies, where a first assembly rigidly holds the elongate flexible shaft and is connected to a second assembly such that rotation of the first assembly about a long axis of the elongate flexible shaft allows rotation of the elongate flexible shaft with respect to the handle, including a third assembly comprised of a rocker mechanism connected to the second assembly by a first pair of pin joints and activation of the first cable to induce joint actuation is achieved by rocking the third assembly with respect to the second assembly about the first pair of pin joints, and further comprising a fourth assembly which includes a plunger mechanism that is connected to the third assembly by assembling it concentrically with a spring with a cylindrical feature of the third assembly, and wherein sliding the fourth assembly along an axis of the cylindrical feature of the third assembly allows a clinician to push and pull the second cable and to open and close the surgical tool at a tip of the flexible elongate flexible shaft.

\* \* \* \* \*